US011986209B2

(12) United States Patent
DiCicco et al.

(10) Patent No.: US 11,986,209 B2
(45) Date of Patent: May 21, 2024

(54) METHODS AND DEVICES FOR CREATION OF COMMUNICATION BETWEEN AORTA AND LEFT ATRIUM

(71) Applicant: Boston Scientific Medical Device Limited, Ballybrit (IE)

(72) Inventors: Matthew DiCicco, Guelph (CA); Gareth Davies, Toronto (CA); Eduardo Moriyama, Richmond (CA); John Paul Urbanski, Toronto (CA)

(73) Assignee: Boston Scientific Medical Device Limited, Ballybrit (IE)

( * ) Notice: Subject to any disclaimer, the term of this patent is extended or adjusted under 35 U.S.C. 154(b) by 397 days.

(21) Appl. No.: 17/185,202

(22) Filed: Feb. 25, 2021

(65) Prior Publication Data
US 2021/0259732 A1   Aug. 26, 2021

Related U.S. Application Data

(60) Provisional application No. 62/981,434, filed on Feb. 25, 2020.

(51) Int. Cl.
*A61B 17/34* (2006.01)
*A61B 17/00* (2006.01)

(52) U.S. Cl.
CPC ...... *A61B 17/3423* (2013.01); *A61B 17/3476* (2013.01); *A61B 2017/00053* (2013.01); *A61B 2017/3425* (2013.01)

(58) Field of Classification Search
CPC .......................................... A61B 2017/00252
See application file for complete search history.

(56) References Cited

U.S. PATENT DOCUMENTS

| 175,254 | A | 3/1876 | Oberly |
| 827,626 | A | 7/1906 | Gillet |
| 848,711 | A | 4/1907 | Weaver |
| 1,072,954 | A | 9/1913 | Junn |
| 1,279,654 | A | 9/1918 | Charlesworth |
| 1,918,094 | A | 7/1933 | Geekas |

(Continued)

FOREIGN PATENT DOCUMENTS

| EP | 2550988 | 1/2013 |
| EP | 3064246 | 9/2016 |

(Continued)

*Primary Examiner* — Nicholas W Woodall
(74) *Attorney, Agent, or Firm* — Nelson Mullins Riley & Scarborough LLP

(57) ABSTRACT

Methods and devices are disclosed for the formation of a communication between the aorta and left atrium. The method includes introducing a puncturing device, positioning the device at a location along the aorta, and advancing the puncturing device to create a pathway. The method may include: a. via an inferior artery, advancing a perforating tip of the puncturing device towards the aorta; b. positioning the perforating tip adjacent a wall of the aorta, proximate the left atrium; and c. advancing the perforating tip to perforate through the wall of the aorta and then through a wall of the left atrium, to create a pathway between the aorta and the left atrium, wherein the creation of the pathway can be confirmed with at least one of fluoroscopy, electro-anatomical mapping, pressure measurement, contrast injection, and echocardiograph.

11 Claims, 21 Drawing Sheets

(56) References Cited

U.S. PATENT DOCUMENTS

| | | | |
|---|---|---|---|
| 1,996,986 A | 4/1935 | Weinberg | |
| 2,021,989 A | 11/1935 | De Master | |
| 2,146,636 A | 2/1939 | Lipchow | |
| 3,429,574 A | 2/1969 | Williams | |
| 3,448,739 A | 6/1969 | Stark et al. | |
| 3,575,415 A | 4/1971 | Fulp et al. | |
| 3,595,239 A | 7/1971 | Petersen | |
| 4,129,129 A | 12/1978 | Amrine | |
| 4,244,362 A | 1/1981 | Anderson | |
| 4,401,124 A | 8/1983 | Guess et al. | |
| 4,639,252 A | 1/1987 | Kelly et al. | |
| 4,641,649 A | 2/1987 | Walinsky et al. | |
| 4,669,467 A | 6/1987 | Willett et al. | |
| 4,682,596 A | 7/1987 | Bales et al. | |
| 4,790,311 A | 12/1988 | Ruiz | |
| 4,790,809 A | 12/1988 | Kuntz | |
| 4,793,350 A | 12/1988 | Mar et al. | |
| 4,807,620 A | 2/1989 | Strul et al. | |
| 4,832,048 A | 5/1989 | Cohen | |
| 4,840,622 A | 6/1989 | Hardy | |
| 4,863,441 A | 9/1989 | Lindsay et al. | |
| 4,884,567 A | 12/1989 | Elliott et al. | |
| 4,892,104 A | 1/1990 | Ito et al. | |
| 4,896,671 A | 1/1990 | Cunningham et al. | |
| 4,928,693 A | 5/1990 | Goodin et al. | |
| 4,936,281 A | 6/1990 | Stasz | |
| 4,960,410 A | 10/1990 | Pinchuk | |
| 4,977,897 A | 12/1990 | Hurwitz | |
| 4,998,933 A | 3/1991 | Eggers et al. | |
| 5,006,119 A | 4/1991 | Acker et al. | |
| 5,019,076 A | 5/1991 | Yamanashi et al. | |
| 5,047,026 A | 9/1991 | Rydell | |
| 5,081,997 A | 1/1992 | Bosley et al. | |
| 5,098,392 A | 3/1992 | Fleischhacker et al. | |
| 5,098,431 A | 3/1992 | Rydell | |
| 5,112,048 A | 5/1992 | Kienle | |
| 5,154,724 A | 10/1992 | Andrews | |
| 5,190,528 A * | 3/1993 | Fonger | A61M 25/01 604/164.11 |
| 5,201,756 A | 4/1993 | Horzewski et al. | |
| 5,209,741 A | 5/1993 | Spaeth | |
| 5,211,183 A | 5/1993 | Wilson | |
| 5,221,256 A | 6/1993 | Mahurkar | |
| 5,230,349 A | 7/1993 | Langberg | |
| 5,281,216 A | 1/1994 | Klicek | |
| 5,300,068 A | 4/1994 | Rosar et al. | |
| 5,300,069 A | 4/1994 | Hunsberger et al. | |
| 5,312,341 A | 5/1994 | Turi | |
| 5,314,418 A | 5/1994 | Takano et al. | |
| 5,318,525 A | 6/1994 | West et al. | |
| 5,327,905 A | 7/1994 | Avitall | |
| 5,364,393 A | 11/1994 | Auth et al. | |
| 5,372,596 A | 12/1994 | Klicek et al. | |
| 5,380,304 A | 1/1995 | Parker | |
| 5,395,341 A | 3/1995 | Slater | |
| 5,397,304 A | 3/1995 | Truckai | |
| 5,403,338 A | 4/1995 | Milo | |
| 5,423,809 A | 6/1995 | Klicek | |
| 5,425,382 A | 6/1995 | Golden et al. | |
| 5,490,859 A | 2/1996 | Mische et al. | |
| 5,497,774 A | 3/1996 | Swartz et al. | |
| 5,499,975 A | 3/1996 | Cope et al. | |
| 5,507,751 A | 4/1996 | Goode et al. | |
| 5,509,411 A | 4/1996 | Littmann et al. | |
| 5,540,681 A | 7/1996 | Strul et al. | |
| 5,545,200 A | 8/1996 | West et al. | |
| 5,555,618 A | 9/1996 | Winkler | |
| 5,571,088 A | 11/1996 | Lennox et al. | |
| 5,575,766 A | 11/1996 | Swartz et al. | |
| 5,575,772 A | 11/1996 | Lennox | |
| 5,599,347 A | 2/1997 | Hart et al. | |
| 5,605,162 A | 2/1997 | Mirzaee et al. | |
| 5,617,878 A | 4/1997 | Taheri | |
| 5,622,169 A | 4/1997 | Golden et al. | |
| 5,624,430 A | 4/1997 | Eton et al. | |
| 5,667,488 A | 9/1997 | Lundquist et al. | |
| 5,673,695 A | 10/1997 | McGee et al. | |
| 5,674,208 A | 10/1997 | Berg et al. | |
| 5,683,366 A | 11/1997 | Eggers et al. | |
| 5,720,744 A | 2/1998 | Eggleston et al. | |
| 5,741,249 A | 4/1998 | Moss et al. | |
| 5,766,135 A | 6/1998 | Terwilliger | |
| 5,779,688 A | 7/1998 | Imran et al. | |
| 5,810,764 A | 9/1998 | Eggers et al. | |
| 5,814,028 A | 9/1998 | Swartz et al. | |
| 5,830,214 A | 11/1998 | Flom et al. | |
| 5,836,875 A | 11/1998 | Webster, Jr. | |
| 5,849,011 A | 12/1998 | Jones et al. | |
| 5,851,210 A | 12/1998 | Torossian | |
| 5,885,227 A | 3/1999 | Finlayson | |
| 5,888,201 A | 3/1999 | Stinson et al. | |
| 5,893,848 A | 4/1999 | Negus et al. | |
| 5,893,885 A | 4/1999 | Webster, Jr. | |
| 5,904,679 A | 5/1999 | Clayman | |
| 5,916,210 A | 6/1999 | Winston | |
| 5,921,957 A | 7/1999 | Killion et al. | |
| 5,931,818 A | 8/1999 | Werp et al. | |
| 5,944,023 A | 8/1999 | Johnson et al. | |
| 5,951,482 A | 9/1999 | Winston et al. | |
| 5,957,842 A | 9/1999 | Littmann et al. | |
| 5,964,757 A | 10/1999 | Ponzi | |
| 5,967,976 A | 10/1999 | Larsen et al. | |
| 5,989,276 A | 11/1999 | Houser et al. | |
| 6,007,555 A | 12/1999 | Devine | |
| 6,009,877 A | 1/2000 | Edwards | |
| 6,013,072 A | 1/2000 | Winston et al. | |
| 6,017,340 A | 1/2000 | Cassidy et al. | |
| 6,018,676 A | 1/2000 | Davis et al. | |
| 6,030,380 A | 2/2000 | Auth et al. | |
| 6,032,674 A | 3/2000 | Eggers et al. | |
| 6,036,677 A | 3/2000 | Javier, Jr. et al. | |
| 6,048,349 A | 4/2000 | Winston et al. | |
| 6,053,870 A | 4/2000 | Fulton, III | |
| 6,053,904 A | 4/2000 | Scribner et al. | |
| 6,056,747 A | 5/2000 | Saadat et al. | |
| 6,063,093 A | 5/2000 | Winston et al. | |
| 6,093,185 A | 7/2000 | Ellis et al. | |
| 6,106,515 A | 8/2000 | Winston et al. | |
| 6,106,520 A | 8/2000 | Laufer et al. | |
| 6,117,131 A | 9/2000 | Taylor | |
| 6,142,992 A | 11/2000 | Cheng et al. | |
| 6,146,380 A | 11/2000 | Racz et al. | |
| 6,155,264 A | 12/2000 | Ressemann et al. | |
| 6,156,031 A | 12/2000 | Aita et al. | |
| 6,171,305 B1 | 1/2001 | Sherman | |
| 6,179,824 B1 | 1/2001 | Eggers et al. | |
| 6,193,676 B1 | 2/2001 | Winston et al. | |
| 6,193,715 B1 | 2/2001 | Wrublewski et al. | |
| 6,210,408 B1 | 4/2001 | Chandrasekaran et al. | |
| 6,217,575 B1 | 4/2001 | Devore et al. | |
| 6,221,061 B1 | 4/2001 | Engelson et al. | |
| 6,228,076 B1 | 5/2001 | Winston et al. | |
| 6,245,054 B1 | 6/2001 | Fuimaono et al. | |
| 6,267,758 B1 | 7/2001 | Daw et al. | |
| 6,270,476 B1 | 8/2001 | Santoianni | |
| 6,283,983 B1 | 9/2001 | Makower et al. | |
| 6,292,678 B1 | 9/2001 | Hall et al. | |
| 6,293,945 B1 | 9/2001 | Parins et al. | |
| 6,296,615 B1 | 10/2001 | Brockway et al. | |
| 6,296,636 B1 | 10/2001 | Cheng et al. | |
| 6,302,898 B1 | 10/2001 | Edwards et al. | |
| 6,304,769 B1 | 10/2001 | Arenson et al. | |
| 6,315,777 B1 | 11/2001 | Comben | |
| 6,328,699 B1 | 12/2001 | Eigler et al. | |
| 6,360,128 B2 | 3/2002 | Kordis et al. | |
| 6,364,877 B1 | 4/2002 | Goble et al. | |
| 6,385,472 B1 | 5/2002 | Hall et al. | |
| 6,394,976 B1 | 5/2002 | Winston et al. | |
| 6,395,002 B1 | 5/2002 | Ellman et al. | |
| 6,419,674 B1 | 7/2002 | Bowser et al. | |
| 6,428,551 B1 | 8/2002 | Hall et al. | |
| 6,450,989 B2 | 9/2002 | Dubrul et al. | |
| 6,475,214 B1 | 11/2002 | Moaddeb | |
| 6,485,485 B1 | 11/2002 | Winston et al. | |

(56) References Cited

U.S. PATENT DOCUMENTS

| | | |
|---|---|---|
| 6,508,754 B1 | 1/2003 | Liprie et al. |
| 6,524,303 B1 | 2/2003 | Garibaldi |
| 6,530,923 B1 | 3/2003 | Dubrul et al. |
| 6,554,827 B2 | 4/2003 | Chandrasekaran et al. |
| 6,562,031 B2 | 5/2003 | Chandrasekaran et al. |
| 6,562,049 B1 | 5/2003 | Norlander et al. |
| 6,565,562 B1 | 5/2003 | Shah et al. |
| 6,607,529 B1 | 8/2003 | Jones et al. |
| 6,632,222 B1 | 10/2003 | Edwards et al. |
| 6,639,999 B1 | 10/2003 | Cookingham et al. |
| 6,650,923 B1 | 11/2003 | Lesh et al. |
| 6,651,672 B2 | 11/2003 | Roth |
| 6,662,034 B2 | 12/2003 | Segner et al. |
| 6,663,621 B1 | 12/2003 | Winston et al. |
| 6,702,811 B2 | 3/2004 | Stewart et al. |
| 6,709,444 B1 | 3/2004 | Makower |
| 6,723,052 B2 | 4/2004 | Mills |
| 6,733,511 B2 | 5/2004 | Hall et al. |
| 6,740,103 B2 | 5/2004 | Hall et al. |
| 6,752,800 B1 | 6/2004 | Winston et al. |
| 6,755,816 B2 | 6/2004 | Ritter et al. |
| 6,811,544 B2 | 11/2004 | Schaer |
| 6,814,733 B2 | 11/2004 | Schwartz et al. |
| 6,820,614 B2 | 11/2004 | Bonutti |
| 6,834,201 B2 | 12/2004 | Gillies et al. |
| 6,842,639 B1 | 1/2005 | Winston et al. |
| 6,852,109 B2 | 2/2005 | Winston et al. |
| 6,855,143 B2 | 2/2005 | Davison et al. |
| 6,860,856 B2 | 3/2005 | Ward et al. |
| 6,869,431 B2 | 3/2005 | Maguire et al. |
| 6,911,026 B1 | 6/2005 | Hall et al. |
| 6,951,554 B2 | 10/2005 | Johansen et al. |
| 6,951,555 B1 | 10/2005 | Suresh et al. |
| 6,955,675 B2 | 10/2005 | Jain |
| 6,970,732 B2 | 11/2005 | Winston et al. |
| 6,980,843 B2 | 12/2005 | Eng et al. |
| 7,022,131 B1 * | 4/2006 | Derowe ............ A61B 17/22012 623/1.11 |
| 7,029,470 B2 | 4/2006 | Francischelli et al. |
| 7,048,733 B2 | 5/2006 | Hartley et al. |
| 7,056,294 B2 | 6/2006 | Khairkhahan et al. |
| 7,083,566 B2 | 8/2006 | Tornes et al. |
| 7,112,197 B2 | 9/2006 | Hartley et al. |
| 7,335,197 B2 | 2/2008 | Sage et al. |
| 7,618,430 B2 | 11/2009 | Scheib |
| 7,651,492 B2 | 1/2010 | Wham |
| 7,666,203 B2 | 2/2010 | Chanduszko et al. |
| 7,678,081 B2 | 3/2010 | Whiting et al. |
| 7,682,360 B2 | 3/2010 | Guerra |
| 7,828,796 B2 | 11/2010 | Wong et al. |
| 7,900,928 B2 | 3/2011 | Held et al. |
| 8,192,425 B2 | 6/2012 | Mirza et al. |
| 8,257,323 B2 | 9/2012 | Joseph et al. |
| 8,337,518 B2 | 12/2012 | Nance et al. |
| 8,388,549 B2 | 3/2013 | Paul et al. |
| 8,500,697 B2 | 8/2013 | Kurth et al. |
| 9,072,872 B2 | 7/2015 | Asleson et al. |
| 9,757,541 B2 | 9/2017 | Haarer |
| 11,339,579 B1 | 5/2022 | Stearns |
| 2001/0012934 A1 | 8/2001 | Chandrasekaran et al. |
| 2001/0021867 A1 | 9/2001 | Kordis et al. |
| 2001/0044591 A1 | 11/2001 | Stevens et al. |
| 2001/0051790 A1 | 12/2001 | Parker |
| 2002/0019644 A1 | 2/2002 | Hastings et al. |
| 2002/0022781 A1 | 2/2002 | McLntire et al. |
| 2002/0022836 A1 | 2/2002 | Goble et al. |
| 2002/0035361 A1 | 3/2002 | Houser et al. |
| 2002/0087153 A1 | 7/2002 | Roschak et al. |
| 2002/0087156 A1 | 7/2002 | Maguire et al. |
| 2002/0111618 A1 | 8/2002 | Stewart et al. |
| 2002/0123749 A1 | 9/2002 | Jain |
| 2002/0147485 A1 | 10/2002 | Mamo et al. |
| 2002/0161424 A1 * | 10/2002 | Rapacki ................ A61F 2/2493 623/1.1 |
| 2002/0169377 A1 | 11/2002 | Khairkhahan et al. |
| 2002/0188302 A1 | 12/2002 | Berg et al. |
| 2002/0198521 A1 | 12/2002 | Maguire |
| 2003/0032929 A1 | 2/2003 | McGuckin |
| 2003/0040742 A1 | 2/2003 | Underwood et al. |
| 2003/0144658 A1 | 7/2003 | Schwartz et al. |
| 2003/0158480 A1 | 8/2003 | Tornes et al. |
| 2003/0163153 A1 | 8/2003 | Scheib |
| 2003/0208220 A1 | 11/2003 | Worley et al. |
| 2003/0225392 A1 | 12/2003 | McMichael et al. |
| 2004/0015162 A1 | 1/2004 | McGaffigan |
| 2004/0024396 A1 | 2/2004 | Eggers |
| 2004/0030328 A1 | 2/2004 | Eggers et al. |
| 2004/0044350 A1 | 3/2004 | Martin et al. |
| 2004/0073243 A1 | 4/2004 | Sepetka et al. |
| 2004/0077948 A1 | 4/2004 | Violante et al. |
| 2004/0116851 A1 | 6/2004 | Johansen et al. |
| 2004/0127963 A1 | 7/2004 | Uchida et al. |
| 2004/0133113 A1 | 7/2004 | Krishnan |
| 2004/0133130 A1 | 7/2004 | Ferry et al. |
| 2004/0143256 A1 | 7/2004 | Bednarek |
| 2004/0147950 A1 | 7/2004 | Mueller et al. |
| 2004/0181213 A1 | 9/2004 | Gondo |
| 2004/0230188 A1 | 11/2004 | Cioanta et al. |
| 2005/0004585 A1 | 1/2005 | Hall et al. |
| 2005/0010208 A1 | 1/2005 | Winston et al. |
| 2005/0049628 A1 | 3/2005 | Schweikert et al. |
| 2005/0059966 A1 | 3/2005 | McClurken et al. |
| 2005/0065507 A1 | 3/2005 | Hartley et al. |
| 2005/0085806 A1 | 4/2005 | Auge et al. |
| 2005/0096529 A1 | 5/2005 | Cooper et al. |
| 2005/0119556 A1 | 6/2005 | Gillies et al. |
| 2005/0137527 A1 | 6/2005 | Kunin |
| 2005/0149012 A1 | 7/2005 | Penny et al. |
| 2005/0203504 A1 | 9/2005 | Wham et al. |
| 2005/0203507 A1 | 9/2005 | Truckai et al. |
| 2005/0261607 A1 | 11/2005 | Johansen et al. |
| 2005/0288631 A1 | 12/2005 | Lewis et al. |
| 2006/0041253 A1 | 2/2006 | Newton et al. |
| 2006/0074398 A1 | 4/2006 | Whiting et al. |
| 2006/0079769 A1 | 4/2006 | Whiting et al. |
| 2006/0079787 A1 | 4/2006 | Whiting et al. |
| 2006/0079884 A1 | 4/2006 | Manzo et al. |
| 2006/0085054 A1 | 4/2006 | Zikorus et al. |
| 2006/0089638 A1 | 4/2006 | Carmel et al. |
| 2006/0106375 A1 | 5/2006 | Werneth et al. |
| 2006/0135962 A1 | 6/2006 | Kick et al. |
| 2006/0142756 A1 | 6/2006 | Davies et al. |
| 2006/0189972 A1 | 8/2006 | Grossman |
| 2006/0241586 A1 | 10/2006 | Wilk |
| 2006/0247672 A1 | 11/2006 | Vidlund et al. |
| 2006/0264927 A1 | 11/2006 | Ryan |
| 2006/0276710 A1 | 12/2006 | Krishnan |
| 2007/0060879 A1 | 3/2007 | Weitzner et al. |
| 2007/0066975 A1 | 3/2007 | Wong et al. |
| 2007/0118099 A1 | 5/2007 | Trout, III |
| 2007/0123964 A1 | 5/2007 | Davies et al. |
| 2007/0167775 A1 | 7/2007 | Kochavi et al. |
| 2007/0185522 A1 | 8/2007 | Davies et al. |
| 2007/0208256 A1 | 9/2007 | Marilla |
| 2007/0225681 A1 | 9/2007 | House |
| 2007/0270791 A1 | 11/2007 | Wang et al. |
| 2008/0039865 A1 | 2/2008 | Shaher et al. |
| 2008/0042360 A1 | 2/2008 | Veikley |
| 2008/0086120 A1 | 4/2008 | Mirza et al. |
| 2008/0097213 A1 | 4/2008 | Carlson et al. |
| 2008/0108987 A1 | 5/2008 | Bruszewski et al. |
| 2008/0146918 A1 | 6/2008 | Magnin et al. |
| 2008/0171934 A1 | 7/2008 | Greenan et al. |
| 2008/0208121 A1 | 8/2008 | Youssef et al. |
| 2008/0243081 A1 | 10/2008 | Nance et al. |
| 2008/0243222 A1 | 10/2008 | Schafersman et al. |
| 2008/0275439 A1 | 11/2008 | Francischelli et al. |
| 2009/0105742 A1 | 4/2009 | Kurth et al. |
| 2009/0138009 A1 | 5/2009 | Viswanathan et al. |
| 2009/0163850 A1 | 6/2009 | Betts et al. |
| 2009/0177114 A1 | 7/2009 | Chin et al. |
| 2009/0264977 A1 | 10/2009 | Bruszewski et al. |
| 2010/0022948 A1 | 1/2010 | Wilson et al. |
| 2010/0087789 A1 | 4/2010 | Leeflang et al. |

(56) References Cited

U.S. PATENT DOCUMENTS

| | | |
|---|---|---|
| 2010/0125282 A1 | 5/2010 | Machek et al. |
| 2010/0168684 A1 | 7/2010 | Ryan |
| 2010/0179632 A1 | 7/2010 | Bruszewski et al. |
| 2010/0191142 A1 | 7/2010 | Paul et al. |
| 2010/0194047 A1 | 8/2010 | Sauerwine |
| 2010/0249908 A1 | 11/2010 | Chau et al. |
| 2011/0046619 A1 | 2/2011 | Ducharme |
| 2011/0087261 A1 | 4/2011 | Wittkampf |
| 2011/0130619 A1 * | 6/2011 | Whisenant ............ A61M 60/88 600/16 |
| 2011/0130752 A1 | 6/2011 | Ollivier |
| 2011/0152716 A1 | 6/2011 | Chudzik et al. |
| 2011/0160592 A1 | 6/2011 | Mitchell |
| 2011/0190763 A1 | 8/2011 | Urban et al. |
| 2012/0109079 A1 | 5/2012 | Asleson |
| 2012/0232546 A1 | 9/2012 | Mirza et al. |
| 2012/0265055 A1 | 10/2012 | Melsheimer et al. |
| 2012/0330156 A1 | 12/2012 | Brown et al. |
| 2013/0184551 A1 | 7/2013 | Paganelli et al. |
| 2013/0184735 A1 | 7/2013 | Fischell et al. |
| 2013/0282084 A1 | 10/2013 | Mathur et al. |
| 2014/0206987 A1 | 7/2014 | Urbanski et al. |
| 2014/0296769 A1 | 10/2014 | Hyde et al. |
| 2015/0157353 A1 | 6/2015 | Lenker et al. |
| 2016/0175009 A1 | 6/2016 | Davies |
| 2016/0220741 A1 | 8/2016 | Garrison et al. |
| 2019/0021763 A1 | 1/2019 | Zhou et al. |
| 2019/0247035 A1 | 8/2019 | Gittard et al. |

FOREIGN PATENT DOCUMENTS

| | | |
|---|---|---|
| JP | 2002532164 | 10/2002 |
| JP | 2007510458 | 4/2007 |
| JP | 2009537255 | 10/2009 |
| JP | 2010227580 | 10/2010 |
| JP | 2011206179 | 10/2011 |
| JP | 2015504328 | 2/2015 |
| JP | 2016530928 | 10/2016 |
| WO | 2005065562 | 7/2005 |
| WO | 2008066557 | 6/2008 |
| WO | 2008079828 | 7/2008 |
| WO | 2011014496 | 2/2011 |
| WO | 2013101632 | 7/2013 |
| WO | 2014182969 | 11/2014 |

\* cited by examiner

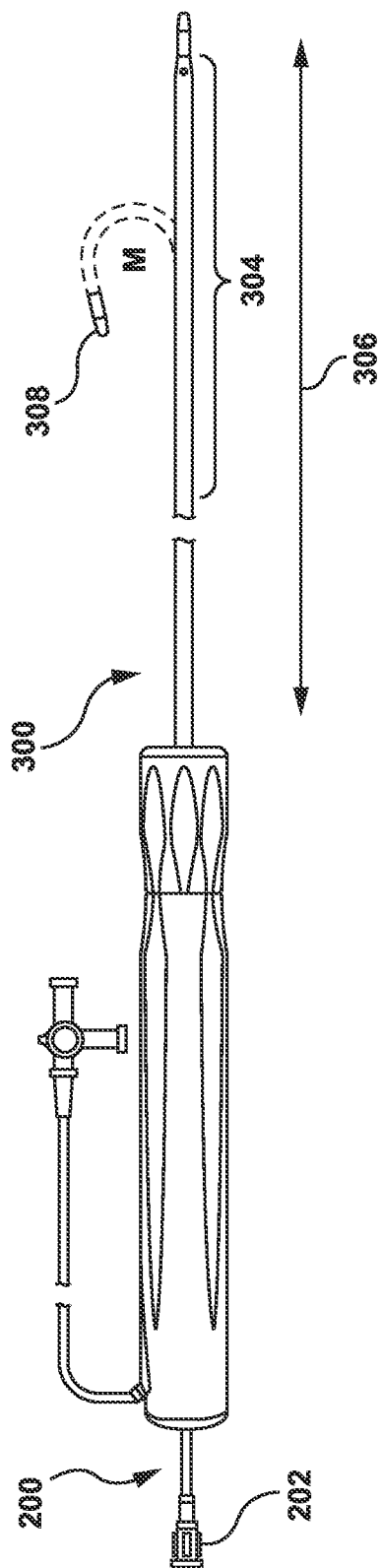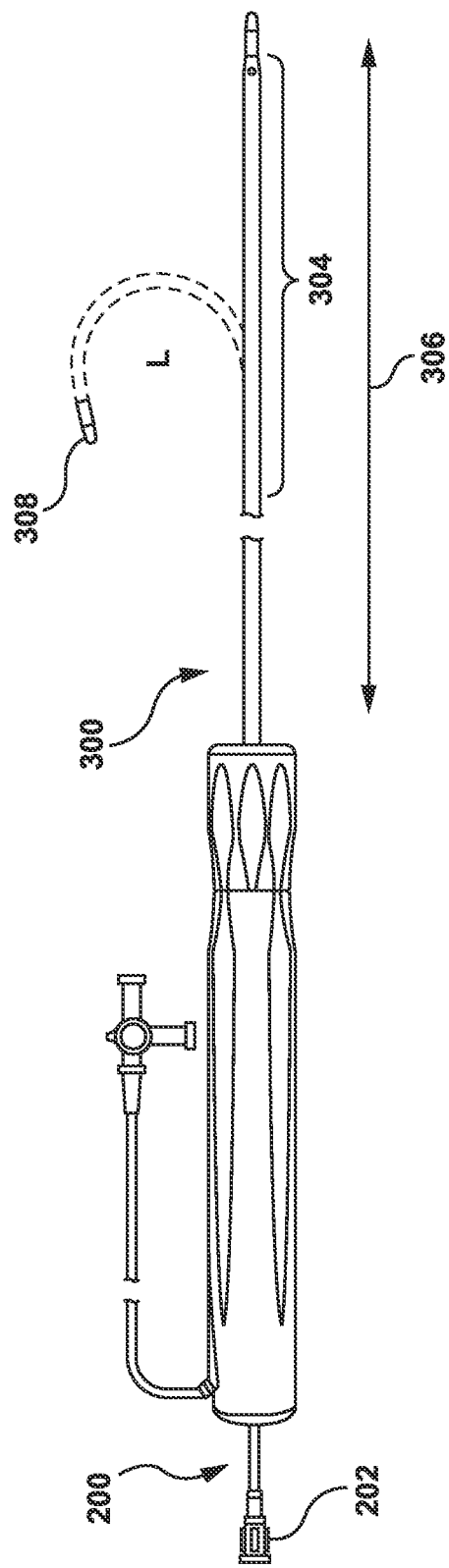

METHODS AND DEVICES FOR CREATION OF COMMUNICATION BETWEEN AORTA AND LEFT ATRIUM

TECHNICAL FIELD

The disclosure relates to systems and methods for creating a puncture in tissue. More specifically, the disclosure relates to a method and device to create a puncture (or a shunt) from the left atrium (LA) to aorta (Ao) or Ao to LA for communication between LA and Ao or Ao and LA.

BACKGROUND OF THE ART

It is often necessary to create perforations between various chambers of the heart and surrounding central vasculature to study etiology, pressure gradients, or enable end-therapy. For example, a left ventricular assist device (LVADs) have been widely used to help heart failure (HF) patients provide sufficient blood flow to peripheral organs, keeping patients alive as a bridge to transplantation or engendering return of native heart function. Percutaneous catheter LVAD support through connection of the left atrium (LA) to the aorta (LA-Ao) is used as a bridge to recovery in heart failure patients specifically because it is non-invasive to ventricular muscle. These LVAD catheters are currently track from the LA through the mitral valve to the LV through the aortic valve, to the aorta. Certain limitations may be associated with this conventional method, such as effusions, valve stenosis, hematoma, and vessel dissection.

SUMMARY

The following summary is intended to introduce the reader to various aspects of the detailed description, but not to define or delimit any invention.

There is a need to create a direct pathway/communication between the aorta and the left atrium while avoiding the mitral and aortic valves and the left ventricle.

Creating a pathway (communication) percutaneously between LA and Ao is significant as the end-therapy device, approach, and selected tools used to create the pathway play a role in optimal site-selection.

There is a need for a streamlined workflow using a puncture device, for example an atraumatic radio frequency (RF) guidewire, to reduce the number of exchanges and optimizes workflow while reducing complications during creation of a LA-Ao communication (e.g., effusions into pericardial space, vessel dissection, hematoma). The ability of the RF wire to navigate tortuous anatomy, puncture at the selected site through steering, deployment of an atraumatic anchor to support dilation and exchange of large sheath systems removes need for exchanging access devices for multiple devices. For example, the RF wire can function in each step of the procedure as a support guidewire.

Methods for creating a pathway between an aorta and a left atrium of a patient's heart are disclosed. According to some aspects, a method for creating a pathway between an aorta and a left atrium of a patient's heart includes: a. via a femoral venous access site and a right atrium, advancing a puncture assembly device towards an interatrial septum, wherein said puncture assembly device comprises a sheath, a dilator, and a flexible puncturing device; b. positioning a perforating tip of puncturing device adjacent an interatrial septum proximate a left atrium; c. advancing the perforating tip to perforate through the interatrial septum creating a pathway between the right atrium and left atrium; d. advancing the puncturing device to the left atrium; e. advancing the sheath and the dilator over the puncturing device through the septum and into the left atrium such that perforating tip of the puncturing device is aligned with a distal tip of the sheath and a distal tip of the dilator, forming said puncturing assembly; f. positioning the puncturing assembly at a target site within the left atrium to gain access to the aorta; and g. advancing the perforating tip of the puncturing device to perforate through the wall of the left atrium and then through a wall of the aorta, to create a pathway between the aorta and the left atrium.

In some examples, the puncturing device is a radiofrequency puncturing device, the perforating tip comprises a radiofrequency perforation electrode, and step g. comprises delivering radiofrequency energy from the radiofrequency perforation electrode while advancing the perforating tip.

In some examples, the method further includes: h. after step g., advancing a dilating tip of the dilator over the perforation device and through the pathway to dilate the pathway between the aorta and the left atrium; and step i. retracting the dilator through the sheath. The sheath can be selected from a steerable sheath, a fixed curve sheath, a small-bore steerable sheath, a large-bore steerable sheath, or a telescoping steerable sheath, and the dilator can be a flexible dilator.

In some examples, the method further includes: j. after step i., delivering a therapeutic device to the pathway via the sheath. Step j. can include positioning a shunt in the pathway or positioning a stent in the pathway.

In some examples, the method may further include: j. via the femoral venous, exchanging the sheath for a large-bore steerable sheath; and i. delivering a therapeutic device to the pathway via a large-bore steerable sheath.

In some examples, the method further includes: h. advancing a snare towards the aorta via an arterial access site (e.g., left or right femoral artery); and i. after step g., snaring the puncturing device with the snare. In some examples, the method further includes: j. after step i., retracting the snare to advance the puncturing device out of the body towards the arterial access site.

In some examples, the method further includes delivering a therapeutic device over the puncturing device towards the pathway, via the arterial access site.

In some examples, at least one of fluoroscopy, angiography, electro-anatomical mapping, intracardiac echocardiography, and transesophageal echocardiography is carried out concurrently with at least one of steps a. to g. In some examples, the method further includes confirming the creation of the pathway with at least one of fluoroscopy, electro-anatomical mapping, pressure measurement, contrast injection, and echocardiography.

According to some aspects, a method for creating a pathway between an aorta and a left atrium of a patient's heart includes: a. via an inferior artery, advancing a perforating tip of a puncturing device towards the aorta; b. positioning the perforating tip adjacent a wall of the aorta, proximate the left atrium; and c. advancing the perforating tip to perforate through the wall of the aorta and then through a wall of the left atrium, to create a pathway between the aorta and the left atrium, wherein the creation of the pathway can be confirmed with at least one of fluoroscopy, electro-anatomical mapping, pressure measurement, contrast injection, and echocardiography.

In some examples, the method further includes: d. via the inferior artery, advancing a dilator over the puncturing device to the aorta; e. after step c., advancing a dilating tip of the dilator over the perforation device and through the pathway to dilate the pathway between the aorta and the left atrium.

In some examples, the dilator can be a steerable dilator or a flexible dilator.

In some examples, the method may further includes: f. via the inferior artery, advancing a sheath over the dilator and the perforation device to the aorta and then to the left atrium; and g. after step e., retracting the dilator through the sheath.

In some examples, the dilator can be a hybrid dilator having features that provide a dual functionality of a sheath and a dilator, and the method may further includes: f. via the inferior artery, advancing the hybrid dilator over the perforation device to the aorta and then to the left atrium. More specifically, the hybrid dilator functions as a single device that removes the need for using conventional sheath/dilator assemblies and eliminates the need for an assembly, resulting in fewer exchanges, and reduced procedure times.

In some examples, the method further includes: d. advancing a snare towards the left atrium via a venous access site, a right atrium and then across an interatrial septum; and e. after step c., snaring the puncturing device with the snare. In some examples, the method further includes: f. after step e., retracting the snare to advance the perforating tip of the puncturing device out of the body towards the venous access site.

In some examples, the method further includes confirming the creation of the pathway between the left atrium and aorta, and/or crossing of the interatrial septum with at least one of fluoroscopy, electro-anatomical mapping (EAM), pressure differentials between the aorta and left atrium, contrast injection, or using intracardiac echocardiography (ICE) or transesophageal echocardiography (TEE).

BRIEF DESCRIPTION OF THE DRAWINGS

The accompanying drawings are for illustrating examples of articles, methods, and apparatuses of the present disclosure and are not intended to be limiting. In the drawings:

FIGS. 3A-3C illustrate a dilator in use with a steerable sheath, in accordance with various embodiments of the present disclosure;

DETAILED DESCRIPTION

Figure 1A:
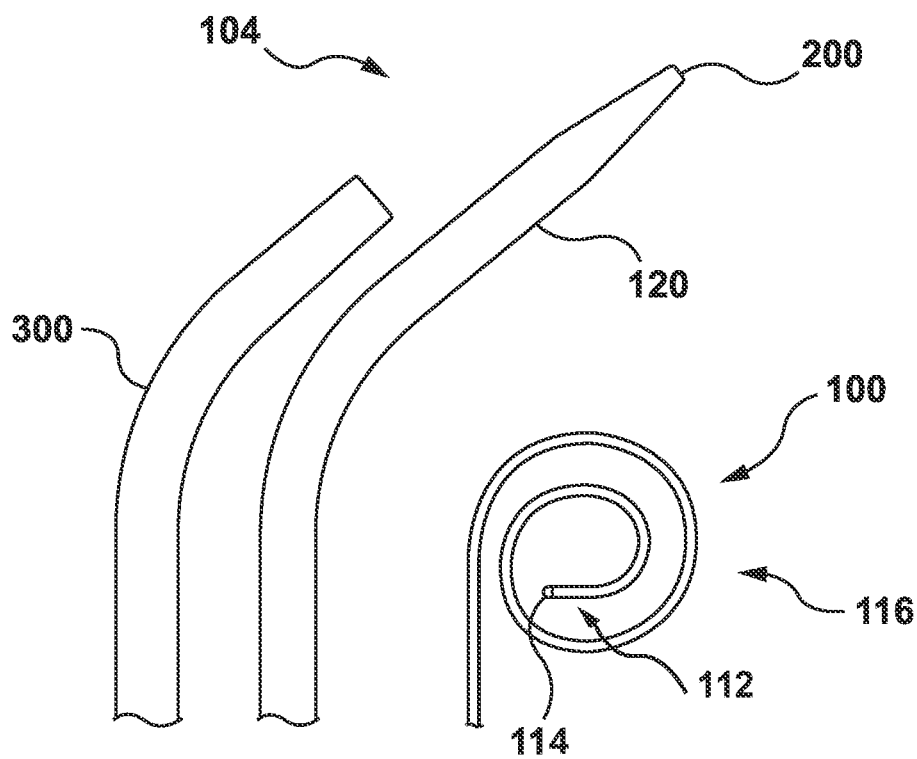
FIGS. 1A and 1B are a schematic view of a puncture assembly device in accordance with an embodiment of the present disclosure.

Various apparatuses or processes or compositions will be described below to provide an example of an embodiment of the claimed subject matter. No example described below limits any claim and any claim may cover processes or apparatuses or compositions that differ from those described below. The claims are not limited to apparatuses or processes or compositions having all the features of any one apparatus or process or composition described below or to features common to multiple or all of the apparatuses or processes or compositions described below. It is possible that an apparatus or process or composition described below is not an embodiment of any exclusive right granted by issuance of this patent application. Any subject matter described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

Generally disclosed herein are methods for carrying out cardiac procedures, and more specifically, cardiac procedures in which a pathway (also referred to as a "communication") is created between the aorta (e.g., the ascending aorta) and the left atrium (LA) of a patient. Such procedures can be carried out, for example, to allow for the insertion of a therapeutic device (e.g., a shunt or a stent) into the pathway, to treat heart defects.

In accordance with some embodiments of the present invention, some details of the devices are disclosed in application number PCT/IB2013/060287 (now publication number WO2015019132), and in application number PCT/IB2017/056777 (now publication number WO2018083599), which are incorporated herein by reference in its entirety.

In one broad aspect, embodiments of the present disclosure provides a method and device to create a communication or pathway from the left atrium (LA) to aorta (Ao) comprising, via a femoral venous access site, advancing a perforating tip of a puncture assembly towards the right atrium, accessing the left atrium via the septum and advancing the perforating tip to perforate through the wall of the left atrium and then through a wall of the aorta, to create a pathway between the aorta and the left atrium. The puncture assembly may include a sheath, a dilator, and a puncturing device usable alone or in combination and configured to facilitate tissue access and puncture at various anatomical locations from desired access sites. The puncturing device is atraumatic and may include one or more sections having sufficient flexibility for accessing the tissue site from the access site while retaining sufficient stiffness to perform one or more additional functions. For example, the puncturing device is capable of navigating vasculature through the femoral artery or femoral vein (for example when using for transseptal puncture) through to the aorta or LA, respectively.

The sheath (such as steerable sheath, fixed curve sheath, or two telescoping steerable sheaths instead of one for enhanced site-selection, small-bore steerable sheath <10 Fr, or large-bore steerable >15 Fr,) and the dilator are advanced over the guidewire (such as a radio frequency wire (RF wire), flexible/steerable needle, mechanical puncture wire, or bovie mechanical guidewire) to reach the target site, for example the left atrium or the aorta. After crossing the target site, the guidewire (for example, an RF wire) is snared, for example with a lasso catheter. The sheath may then be removed leaving the guide wire (such as an RF wire) within the LA for advancing end-therapy devices over the wire. In some instances, the access sheath may be advanced into the LA if the access sheath can support delivery of end therapy devices. In some cases, the selected end-therapy may not fit in the arterial vasculature chosen. A larger bore pathway to the target site can be created through the puncture to facilitate large-bore access into the LA-Ao and the selected end-therapy can then be tracked over the wire up the femoral artery or femoral vein and through the puncture.

In some embodiments, a vascular snare or lasso catheter is used. The lasso catheter comprise an elongated sheath connected to a handle at the proximal end. One or more loops are connected to the distal-end portion of the lasso catheter. The one or more loops may be opened and closed by manipulating the proximal end. When the one or more loops are open, a device may be ensnared within the loop. Successful ensnarement is usually confirmed through imaging such a fluoroscopy. Once ensnarement is achieved, the device can be retracted by the lasso.

In further instances, the wire may be externalized to support advancement of end-therapy devices. The access site to externalize out may be the femoral artery, common carotids, or femoral vein. With an externalized wire of sufficient length, it can be used to support stiffer end-therapy devices. In some cases, the selected end-therapy may not fit in the arterial vasculature chosen. To facilitate large-bore access into the LA-Ao communication (pathway) made, it can then be tracked over the RF wire up the femoral artery or femoral vein and through the puncture.

Access to the vasculature for creation of the communication (pathway) may be achieved from a femoral approach through the femoral vein or femoral artery. These specific embodiments can also be utilized for other approaches from central vasculature or for the creation of communication between other heart chambers and heart spaces with the intent of facilitating study or placement of end-therapy devices.

As a feature of this aspect, the site of puncture can be determined through several visualization methods, including but not limited to: (1) fluoroscopy through the use of RO (radiopaque) markers on the sheath and RF wire system; (2) electro-anatomical mapping for real-time placement of the RF wire and sheath with targets pre-determined on CT or in real-time (in real-time, the lasso catheter or guidewire with one or more electroanatomical (EAM) markers can be placed in the LA or Ao as a target for positioning and relative orientation; and (3) echogenic markers or features on either the RF wire or the supporting catheter can enable use of ICE or TEE for delineation of etiology and optimal target site to avoid damaging surrounding vasculature. Support and etiology of surrounding vasculature can also be used to interpret site selection. For creating the communication to or from the ascending aorta, for example, locating above the sinotubular junction (STJ) can aid in alignment with the LA. In cases where end-therapy sheaths need to be exchanged for the catheter system over the guidewire, such as an RF wire which is advanced during RF energy application, it can be useful to prevent un-intended dilation with the catheter system. While tenting tissue during site selection, the dilator (preferably sufficiently flexible dilator) can be retracted into the flexible sheath until the dilator and the sheath tip are aligned. As the flexible dilator easily conforms to the shape of the sheath, this can be completed without losing the optimal puncture location selected, resulting in decreased pressure on target tissue from sheath tip.

In some such examples, confirmation of access into Ao from LA or from the LA to Ao can be determined through several methods, including but not limited to: (1) fluoroscopy through the use of RO markers on the sheath and RF wire system; (2) electro-anatomical mapping for real-time placement of the guidewire, for example RF wire, and sheath with targets pre-determined on CT or in real-time (in real-time, a catheter or guidewire with one or more EAM markers can be placed in the LA or Ao as a target for positioning and relative orientation); (3) pressure differentials from the Ao to the LA and vice-versa; (4) contrast injection; and (5) echogenic markers or features on either the coil or the catheter can enable use of ICE or TEE for confirmation of location.

In an embodiment, an assembly is provided for puncturing tissue, where the assembly comprises a puncturing device for puncturing tissue. The puncturing device preferably comprises an atraumatic tip. Preferably, the atraumatic tip comprises an energy delivery device such as an electrode, capable of delivering radiofrequency energy to the target tissue, thereby creating a puncture in the tissue. In some examples, the puncturing device may be flexible, enabling the puncturing device to also be used as an exchange or guidewire. The assembly additionally comprises ancillary devices, such as a sheath and/or dilator, for supporting the flexible puncturing device. The sheath and/or dilator are operable to be selectively usable with the flexible puncturing device. In some examples, the flexible puncturing device is an energy-based device for delivering energy to the tip of the puncturing device in order to puncture the septum. In some embodiments, the flexible puncturing device has a lumen and one or more apertures. The lumen and aperture may combine to form a pressure transmitting lumen. The flexible puncturing device may be operable to be coupled to a pressure sensing mechanism, such as a pressure sensor, to measure the pressure transmitted through the lumen. In some embodiments, fluid (such as imaging or contrast fluid) is injected through the lumen and one or more apertures.

The assembly enables the flexible puncturing device to be usable independently from the ancillary devices as an exchange or guidewire during a portion of the procedure and to be usable in co-operation with other devices for puncturing tissue during another portion of the procedure. This reduces the number of exchanges needed by allowing the flexible puncturing device to be used for puncturing tissue, and as an exchange wire. The ancillary devices facilitate positioning of the energy delivery portion of the puncturing device against the desired target tissue location and may additionally reduce procedure complexity and enhance procedural efficiency.

Figure 1B:
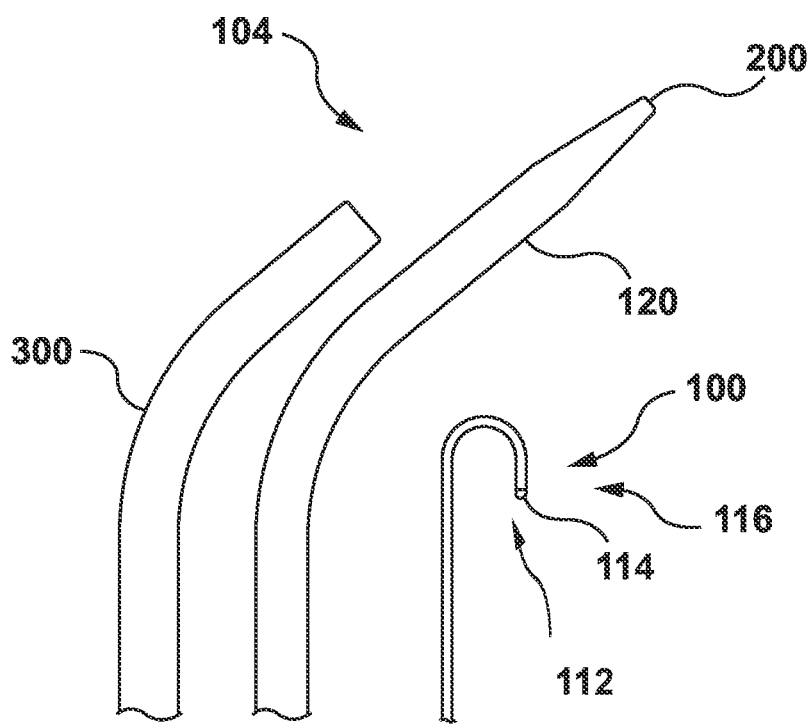

Referring to FIGS. 1A and 1B, illustrations of a puncture assembly device 104 are provided that incorporates embodiments of devices that may be utilized during the procedure disclosed herein. The assembly 104 can be used for puncturing tissue such as interatrial septum and/or for creating a pathway or communication between left atrium and aorta (from left atrium (LA) to aorta (Ao) or Ao to LA). The assembly 104 comprises a tissue puncturing device 100, and ancillary device. In some examples, the ancillary device comprises a sheath 300 and a dilator 200 that are selectively usable with the tissue puncture device 100. In some examples, the tissue puncturing device 100 is substantially flexible, that can be maneuvered to the desired target location and/or that can be used as an exchange wire or guide wire without buckling or dislodging during exchanges. In some examples, the substantially flexible tissue puncture device 100 comprises a distal portion (section) 116 and a substantially atraumatic distal tip (perforating tip)112. The distal tip 112 may further comprise an energy delivery device 114 that is operable to deliver energy to puncture tissue. In some examples, the energy delivery device 114 can be an electrode, capable of delivering radiofrequency energy for puncturing a tissue. In an alternative embodiment, the substantially flexible tissue puncturing device 100 may comprise a sharp distal tip, which may be used to mechanically puncture the tissue.

In some examples, the distal portions (sections) 116 of the assembly 104 comprise a pigtail or J-tip configuration, as shown in FIGS. 1A and 1B. These configurations facilitate anchoring of the puncture device 100, for example after puncture. In some examples, the puncture device 100 comprises a radiofrequency (RF) wire that has an electrode at the distal tip (perforating tip)112 for delivering radiofrequency to puncture a tissue. In some examples, the RF wire is a flexible wire which is generally electrically insulated, save for selected distal regions with an electrode at the perforating tip 112. In an alternative embodiment, the puncture device 100 may comprise a sharp perforating tip 112 which relies on the application of mechanical force to puncture the tissue. In another embodiment, the puncture device 100 may be a steerable needle or a steerable power catheter.

In some embodiments of the puncture assembly device 104, the dilator 200 and sheath 300 each defines a respective lumen through which devices may be inserted (as shown in FIGS. 1A and 1B).

In some embodiments, the sheath 300 is a steerable sheath. In some embodiments, the steerable sheath is unidirectional, i.e., it allows deflection in a single direction. In other embodiments, a bi-directional sheath may be used. Alternately, in some embodiments, a fixed curve sheath may be utilized in place of an articulating sheath, depending on the tortuosity of the vasculature.

In some examples, the dilator 200 provides stiffness to the puncture assembly device 104 to facilitate force transmission to a distal end of the puncture assembly device 104. In other examples, the sheath 300 may be used with the dilator 200 to provide stiffness to the puncture assembly device 104 to enable force or torque to be transmitted to a distal end of the puncture device 100. In some such examples, the sheath 300 may be coupled to the dilator 200 which enables force and/or torque transmission using one or more of the components (i.e., the sheath 300 or the dilator 200). In other words, the user may just manipulate the sheath 300 or the dilator 200) and the puncture device 100 will follow the guidance and/or direction of the sheath 300 or the dilator 200.

In some embodiments, the dilator 200 is a flexible dilator used with a steerable sheath 300 to access a region of tissue within a patient's body. The steerable sheath 300, defining a lumen therethrough for receiving the dilator, has a range of deflection angles and to achieve a range of curvature upon actuation. The dilator 200 includes a substantially flexible or soft section that provides minimal resistance to deflection and is operable to be deflected under guidance to allow the dilator 200 to reach a desired site within a region of tissue within the patient's body to facilitate advancement of the distal end region. The flexible region allows the dilator 200 to conform to the curvature of the steerable sheath 300 that is achieved through actuation of the steerable sheath. In some embodiments, the distal end of the dilator 200 extends beyond the distal end of the sheath 300 to improve access to the target tissue within the patient's body.

In an embodiment, the dilator 200 is for use with an ancillary device such as a steerable sheath to access a region of tissue or tissue site within a patient's body, the steerable sheath defining a lumen therethrough for receiving the dilator and having a range of deflection angles. The dilator 200 comprises a rigid distal end region; and a flexible intermediate region. The dilator 200 can be configured in a such a way that, when the dilator is inserted into the lumen of the steerable sheath, the location of the flexible intermediate region corresponds to a location of a region of the steerable sheath that is amenable to deflection (also referred to as a "curvature-imparting region" or an "articulating region"). The dilator 200 may further comprise a rigid distal end region having a rigidity greater than the flexible intermediate region to enable the dilator to advance through tissue.

In the aforementioned embodiments, the dilator 200 is structured in such a way that, during use, the flexible intermediate region of the dilator is configured to provide minimal resistance to deflection so as to allow the deflectable region of the steerable sheath to deflect, thereby allowing the steerable sheath to reach a desired deflection angle from said range of deflection angles, to position the dilator rigid distal end region at a desired location within the region of tissue, allowing the dilator rigid distal end region to facilitate advancement of the dilator there-through.

In the embodiments, the dilator 200 described above are sufficiently flexible to allow the ancillary device to guide and position the dilator and/or additional devices in a wide array of patient anatomies. Embodiments of the dilator 200 accomplish this function by providing a flexible intermediate region having reduced stiffness. The location of the flexible region, when the dilator is inserted into/through the ancillary device, corresponds to a region of the ancillary device that is amenable to deflection or has a particular shape or curve, whereby the flexibility of the dilator at that location helps to ensure that the dilator does not substantially impair the ability of the ancillary device to retain, maintain or reach its intended shape or curvature. In some embodiments, the dilator 200, while being sufficiently flexible along the intermediate region, has sufficient stiffness along a distal end region to allow the dilator to be tracked or advanced across tissue for dilating a perforation or puncture at the desired target tissue site.

Figure 2A:
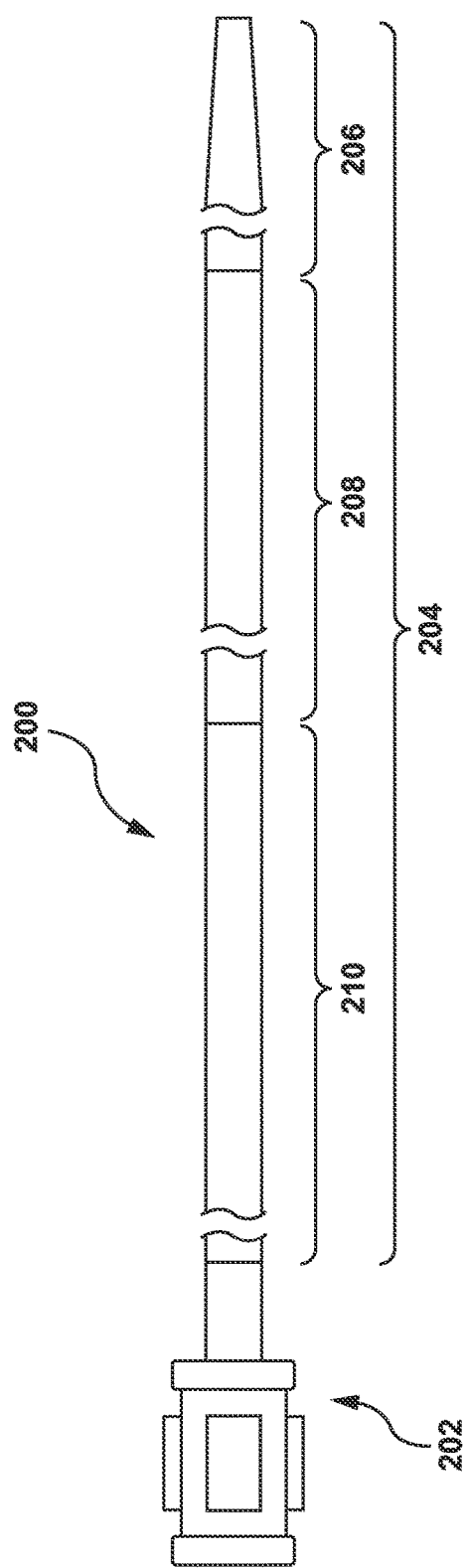
FIG. 2A is a perspective view of a dilator in accordance with an embodiment of the present disclosure.
Figure 2B:
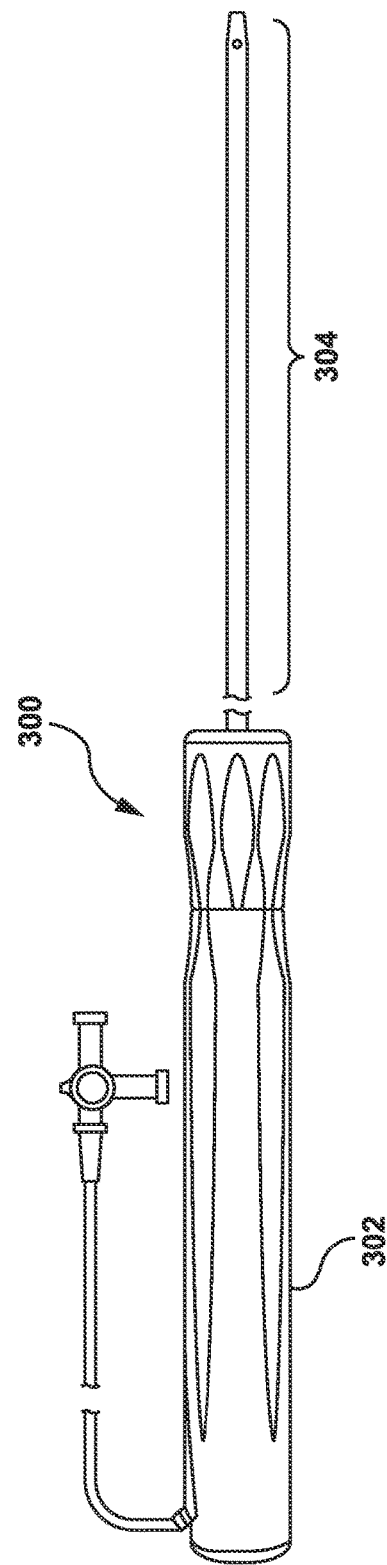
FIG. 2B is a perspective view of a steerable sheath in accordance with an embodiment of the present disclosure.

In accordance with another embodiment, as shown in FIG. 2A, a flexible dilator 200 is disclosed for use with a steerable sheath 300 (shown in FIG. 2B) to access a region of tissue within a patient's body. The steerable sheath 300 has a range of deflection angles and can achieve a range of curvatures upon actuation. Referring again to FIG. 2A, the dilator 200 comprises a dilator hub 202 that is coupled to an elongate member 204 that comprises regions of varying flexibility including an intermediate region 208 that terminates in a distal end region 206. In accordance with an embodiment of the present invention, the intermediate region 206 is a substantially flexible or soft section that provides minimal resistance to deflection and is operable to be deflected under guidance to allow the dilator 200 to reach a desired site within a region of tissue within the patient's body to facilitate advancement of the distal end region 206 there-through. The flexible intermediate region 208 allows the dilator 200 to conform to the curvature of the steerable sheath 300 that is achieved through actuation of the steerable sheath 300. Thus, in some embodiments, as outlined herein, the flexible intermediate region 208 does not inhibit the range of motion of the steerable sheath 300.

Additionally, the elongate member 204 of the dilator 200 further comprises a distal end region 206 that is formed distally adjacent to the flexible intermediate region 208, such that the flexible intermediate region 208 continues distally until (and terminates at) a proximal boundary or edge of the distal end region 206. In other words, the distal end region 206 extends proximally from the distal edge of the dilator 200 until a distal edge of the flexible intermediate region 208. The distal end region 206 has a stiffness or rigidity that is greater than the flexible intermediate region 208 to facilitate advancement of the dilator 200 through the tissue once the dilator 200 has been positioned at the desired tissue site, such as a desired puncture site. The stiff or substantially rigid distal end region 206 provides enhanced pushability and may prevent deformation thereof during advancement of the distal end region 206 through the tissue, for example at the puncture site to dilate the puncture site.

As outlined previously, the dilator 200 is usable with a steerable sheath 300 to access a region of tissue within a patient's body. The steerable sheath 300 may be of the type shown in FIG. 2B comprising an articulating portion or deflectable region 304 that is amenable to deflection upon actuation of a steerable actuation mechanism for example such as a knob of a handle 302. In use, the dilator 200 is inserted within the steerable sheath 300 such that a location or position of the flexible intermediate region 208 of the dilator 200 corresponds to the articulating portion or deflectable region 304 of the steerable sheath. This enables the steerable sheath 300 to reach its allowable range of curvatures or deflection, upon actuation, as minimal resistance is introduced by the dilator 200. In other words, the flexible intermediate region 208 of the dilator does not impart rigidity to the steerable sheath 300 as the dilator 200 is being steered by the steerable sheath 300. This enables the steerable sheath 300 to position the distal end region 206 of the dilator 200 at a desired target location within a region of tissue such as at a desired puncture location or site to enable the distal end region 206 to subsequently advance there-through while dilating the puncture site.

In a specific embodiment, an 8.5 French steerable sheath 300 with a 72 cm usable length and an 8.5 French dilator 200 with a usable length of 95 cm can be used. The dilator 200 tapers down to an outer diameter (OD) of about 0.046" (about 1.2 mm) and an inner diameter (ID) of about 0.036" (about 0.9 mm) at the distal tip.

Figure 2C:
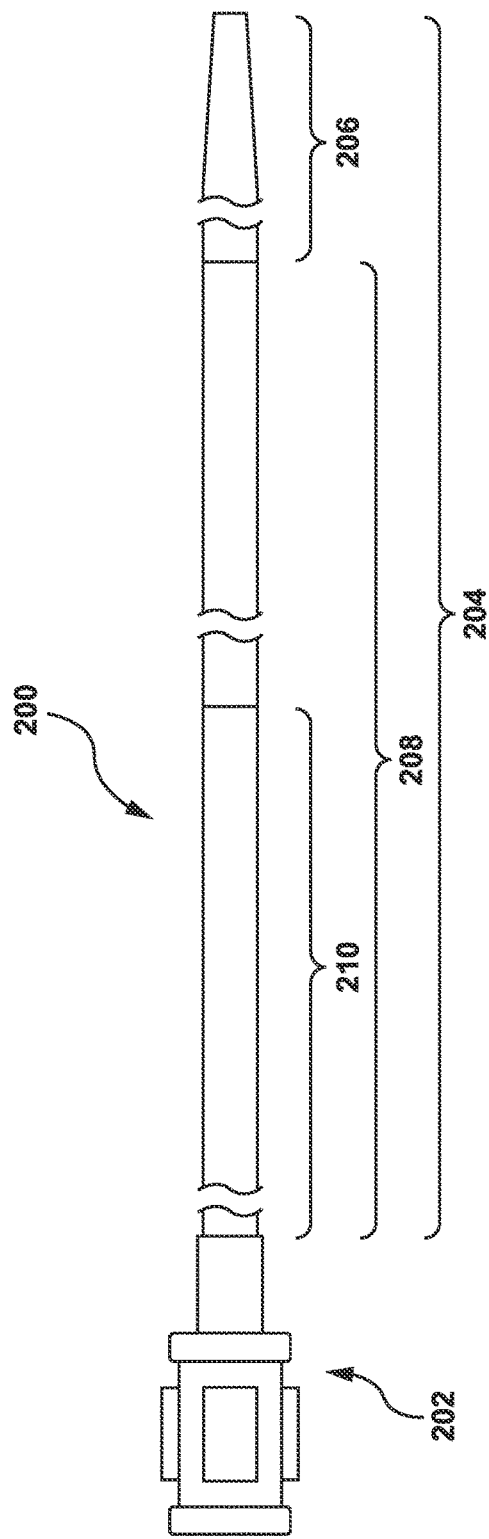
FIG. 2C is a perspective view of a dilator in accordance with an alternate embodiment of the present disclosure.

In one embodiment, with reference to FIG. 2A, dilator 200 further comprises a proximal region 210 that forms a part of elongate member 204 of dilator 200. The proximal region 210 extends proximally from the flexible intermediate region 208. More specifically, the proximal region 210 extends proximally from a proximal boundary of the flexible intermediate region 208 and may extend until the dilator hub 202. In some embodiments the proximal region 210 may also be formed from a flexible material and exhibits flexibility. Alternatively, in other embodiments, as shown in FIG. 2C, the flexible intermediate region 208 may extend along the proximal region 210 and may include the proximal region 210. In some such embodiments, the flexible intermediate region 208 may have varying regions of flexibility.

Figure 3A:
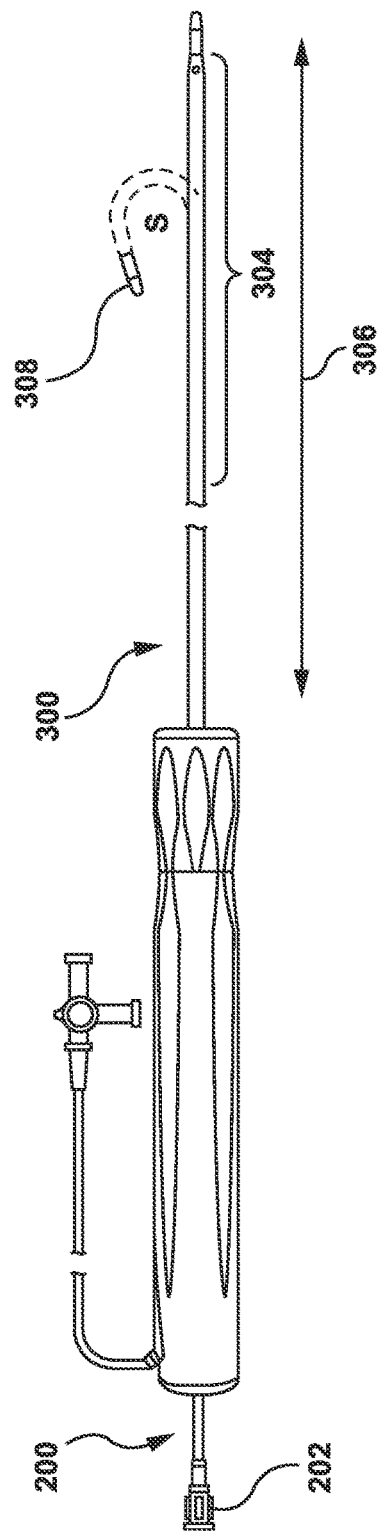

With reference now to FIGS. 3A-3C, various embodiments of a steerable sheath 300 are shown with the dilator 200 inserted there-through. In some embodiments, once the dilator 200 has been inserted through the steerable sheath 300, the dilator 200 extends by a distance, for example about 3 cm, distally beyond the distal end or tip of the steerable sheath 300 (more specifically, beyond the distal end/edge of the steerable sheath 300). In some embodiments, the dilator extends by between about 2 cm to about 4 cm beyond the distal edge of the steerable sheath 300. In some embodiments, the steerable sheath 300 has a usable length 306 that is between about 71 cm to about 89 cm.

In one specific example, with reference now to FIG. 3A, the steerable sheath 300 is an 8.5 French unidirectional steerable sheath, that has a deflectable region or articulating portion 304 operable to adopt a curve S having an angle of about 180 degrees and a having a radius of curvature of about 8.5 mm. Alternatively, in the example as shown in FIG. 3B, the deflectable region or articulating portion 304 of the steerable sheath 300 is operable to adopt a curve M having a radius of curvature of about 11 mm. In another example as shown in FIG. 3C, the deflectable region or articulating portion 304 of the steerable sheath 300 is operable to adopt a curve L, having a radius of curvature equal to about 25 mm.

In one embodiment, the dilator 200 is usable with an ancillary device such that it allows the ancillary device to maintain or reach its intended shape or curvature in order to access a desired tissue site within a region of tissue within a patient's body. The dilator 200 may be of the type described herein above, that comprises a rigid distal end region 206 and a flexible intermediate region 208 terminating at the distal end region 206, with the rigid distal end region 206 having a rigidity greater than the flexible intermediate region 208 to enable the dilator 200 to advance through tissue. The dilator 200 is configured for use in conjunction with the ancillary device such that during use, the flexible intermediate region 208 corresponds to a region of the ancillary device that is functional for imparting or providing a curvature. In one particular example, the dilator 200 is advanced over or through the ancillary device such that such that during use the flexible intermediate region 208 of the dilator 200 does not affect the region of the ancillary device that is functional for imparting a curvature, allowing the ancillary device to substantially maintain or reach its intended position or shape in order to position the dilator rigid distal end region 206 at a desired location within the region of tissue.

In one such example, the ancillary device comprises a steerable device such as a sheath, catheter or guidewire that is steerable, where the ancillary device is functional for imparting a curvature by actuation of the ancillary device. When in use in conjunction with the dilator 200, the flexible intermediate region 208 of the dilator does not inhibit or prevent the ancillary device from reaching its intended curvature upon actuation to position the dilator distal end region 206 at a desired location. In another example, the ancillary device comprises a telescoping steerable sheath to enhance target site-selection.

Alternatively, in some embodiments, the ancillary device comprises a fixed curve device such as a fixed curve sheath that has a preformed curve. Similar to embodiments discussed previously herein, the fixed curve sheath is usable with the dilator 200 and during use the flexible intermediate region 208 of the dilator 200 does not affect the preformed curvature of the sheath, thus allowing the sheath to position the rigid distal end 206 of the dilator 200 at the desired location within the region of tissue. Furthermore, the use of the dilator 200, in accordance with an embodiment of the present invention, may prevent the need for over curving the sheath in anticipation of a substantial decrease in curvature of the sheath once the dilator 200 there-through.

In some embodiments, it may be desirable to use a hybrid dilator comprising features that provide a dual functionality of a sheath and a dilator. The hybrid dilator provides the smoothness of a standard dilator with the control of a steerable sheath. More specifically, the hybrid dilator functions as a single device that removes the need for using conventional sheath/dilator assemblies and eliminates the need for an assembly, resulting in less waste, fewer exchanges, and reduced procedure times. The hybrid dilator may comprise a sheath-like handle with familiar torque and tactile control. For example, the hybrid dilator comprises a proximal portion of a sheath hub with an actuation mechanism to steer the distal portion. The shaft extending from the hub is similar to that of a dilator wherein the distal tip comprises a tapered portion which may be used to dilate the puncture.

As outlined above, in some embodiments described herein above, the dilator 200 comprises varying regions of flexibility (i.e., rigid and flexible regions) to define a hybrid medical device. Since the dilator 200 comprises a substantially constant OD and ID and thus substantially constant wall thickness along its length, the behavior of the various regions, in terms of rigidity, is governed by the stiffness of the materials used. For example, the higher the stiffness of a material, the greater the rigidity, and the lower the stiffness of the material the lower the rigidity. Alternatively, in other embodiments, a single material may be used to form the dilator where the varying regions of flexibility are provided by varying the wall thickness along the respective regions. For example, an HDPE dilator may be provided with a relatively thin wall thickness along the flexible intermediate region and a relatively thicker wall thickness along the distal end region, in order to provide a dilator with the functionality described previously hereinabove.

In accordance with embodiments of the present invention, as described hereinabove, FIGS. 1A and 1B, 2A to 2C, and 3A to 3C illustrate embodiments of a medical device operable to be guided to a tissue site to puncture tissue and to function as a rail for installing devices thereupon. Such embodiments provide efficiencies to medical procedures in which they are utilized as they perform multiple functions and thereby reduce the amount of device exchanges that need to be performed. The "hybrid" medical devices further facilitate the access and puncture of a tissue site upon insertion at a particular access site on a patient's body.

FIGS. 1A and 1B illustrate embodiments of a substantially flexible energy based puncturing device such as an RF wire that is sufficiently flexible to enable access to heart tissue, such as from the left atrium (LA) to aorta (Ao) or Ao to LA for communication between LA and Ao or Ao and LA or a septum, from, for example, a transhepatic approach. An active region at the distal tip (perforating tip) 112 is operable to deliver energy for puncturing tissue (such as interatrial septum or a tissue between aorta and left atrium to create a puncture site therethrough which the RF wire can be advanced, for example to enter the left atrium from right atrium). In a specific embodiment the RF wire has an outer diameter (OD) of 0.035" and a wire length of 180 cm. In another example, the RF wire has an outer diameter (OD) of 0.032". In a further example, the RF wire has a radiopaque marker.

FIG. 1A shows a specific embodiment of a pigtail RF wire where the distal section 116 is biased to form a coil for anchoring the RF wire beyond the puncture site. FIG. 1B shows an example of a J-tip RF wire where the distal section 116 substantially forms a "J". In some examples, when distal section 116 is advanced out of a dilator and beyond the septum or aorta, the biased curves act as an anchor in the left atrium, providing a rail into the left atrium. In an alternative embodiment, the distal portion of the RF wire may comprise an anchoring element which would help anchor the RF wire at a desired location.

Creating Pathway (Communication) Between the Left Atrium and Aorta via Inferior Approach Access to the vasculature for creation of the pathway is achieved from inferior approach through the right atrium and then the interatrial septum. The vasculature may be accessed using traditional access procedures, such as the Seldinger technique, with the placement of a hemostatic valve (known and used in medical procedures requiring the insertion of a catheter into the vascular system of a patient). A puncturing device 100 may then be introduced into the patient's vasculature and then to the right atrium which would provide the most direct path to the first target puncture site of the interatrial septum. In the following embodiments, the puncturing device 100 is illustrated as a flexible puncturing device 100, such as a flexible puncturing guidewire; however, the puncturing device may be any alternative device used for puncturing tissue, such as a steerable needle, a steerable power catheter or a mechanical puncturing wire.

Referring now to FIGS. 4A to 16, a method for carrying out a cardiac procedure, and specifically for creating a pathway between an aorta and a left atrium via a venous access site (such as the femoral vein, the hepatic vein, etc.,) or arterial access site (e.g., left or right femoral artery) will be described. The method will be described with regard to the assembly device 104 shown in FIGS. 1A and 1B; however, the method is not limited to the assembly device 104.

In some examples of this method, FIGS. 4A, 4B, 5, 6, 7A, 7B, 7C, 8A, and 8B illustrates steps in which a pathway (communication) is created between left atrium and aorta via a venous access site (via the femoral vein)—that is, the left atrium can be approached via inferior vena cava (IVC) 706, the right atrium 704—for creating transseptal perforation and advancing to the left atrium 512, and then a perforation can be created in the wall of the left atrium (adjacent to ascending aorta) and then into the wall of aorta 504.

Figure 4A:
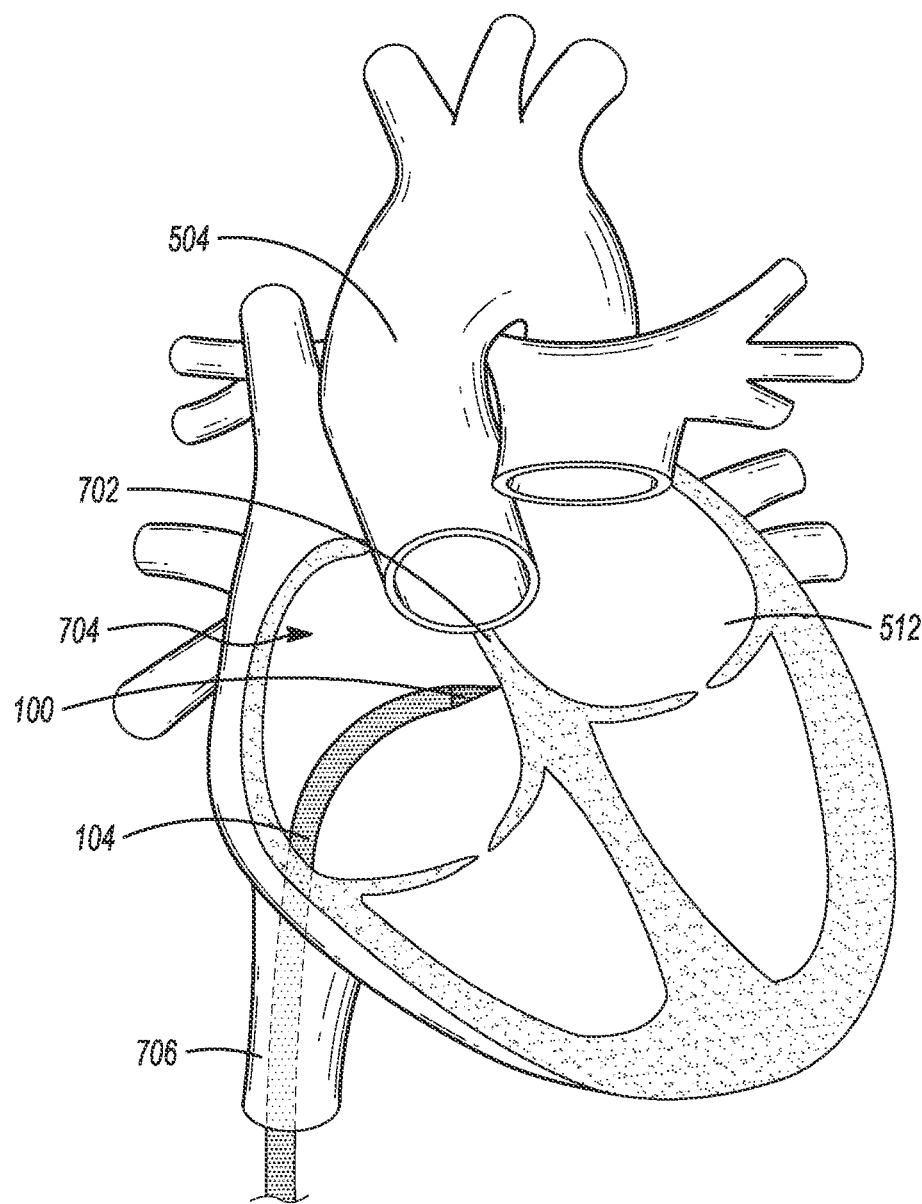
FIGS. 4A, 4B, 5, 6, 7A, 7B, 7C, 8A, and 8B illustrates the steps of a method for accessing an aorta via a left atrium, in accordance with an embodiment of the present disclosure.

Referring to FIG. 4A, as a first step, the inferior vena cava (IVC) 706 is percutaneously accessed (e.g., using a procedure such as a Seldinger technique) and the perforating tip (distal tip) 112 of the puncturing device 100 can be advanced into the right atrium and towards the interatrial septum 702. The puncturing device 100 is a flexible puncturing device 100, such as a flexible puncturing guidewire; however, the puncturing device 100 may be any alternative device used for puncturing tissue, such as a steerable needle, a steerable power catheter or a mechanical puncturing wire. The assembly 104 of the sheath 300, dilator 200, and flexible puncturing device 100 are positioned within the right atrium and directed to a target site of interatrial septum. Once the assembly 104 is directed at the target puncturing site of the septum, the assembly 104 may tent the interatrial septum 702.

Figure 4B:
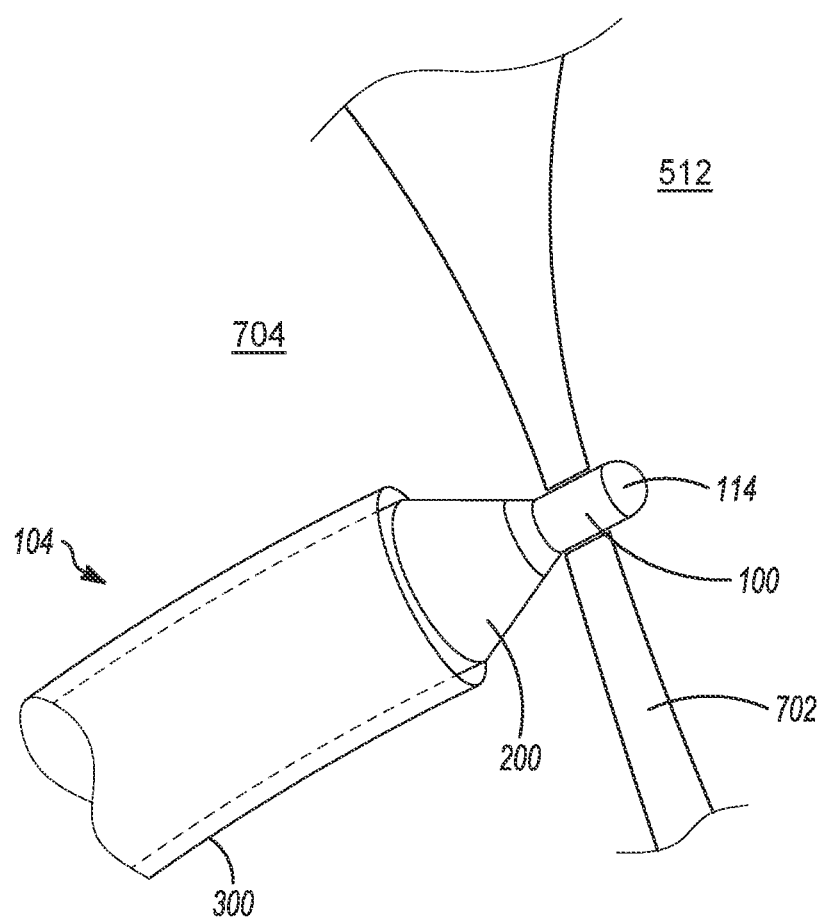

Referring to FIG. 4B, radiofrequency energy is then applied to the flexible puncturing device 100 and delivered to the distal tip (perforating tip) 112 (not shown) via the energy delivery device 114 for puncturing the septum thereby creating a hole or pathway in the interatrial septum 702 between the right atrium and left atrium. The flexible puncturing device 100 is advanced through the transseptal perforation at location into the left atrium. Alternatively, the puncturing device 100 may comprise a sharp distal tip 112 which may be used to mechanically puncture the interatrial septum 702.

Figure 5:
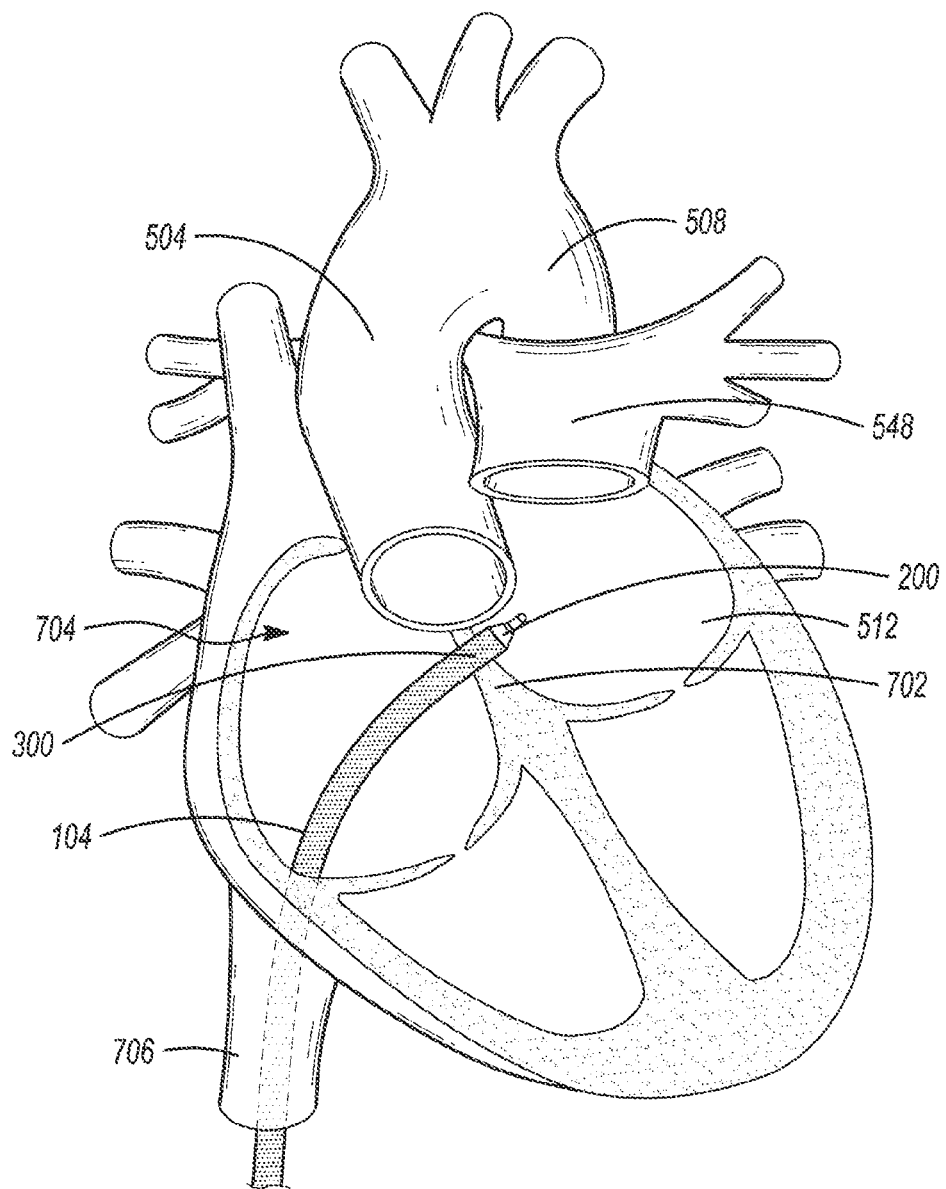

With the flexible puncturing device 100 situated within the left atrium 512, the dilator 200 and the sheath 300 are advanced along flexible puncturing device 100 into the left atrium 512 until the distal tip of the flexible puncturing device 100 is aligned with the distal tip of the dilator 200, as shown in FIG. 5. In some examples, the dilator 200 may be advanced first, over the flexible puncturing device 100 through the puncture site to dilate the tissue and enlarge the puncture site for smooth advancement of the sheath 300 over the dilator 200.

In some examples, the target site of the transseptal perforation, advancement of the of puncturing device 100 from right atrium to left atrium, and the position of the perforating tip 112 of puncturing device 100 can be confirmed using fluoroscopy (e.g. in examples wherein the puncturing device 100 or the assembly 104 includes one or more radiopaque markers or features), angiography, electro-anatomical mapping (EAM) (e.g. to confirm real-time positioning of the perforating tip 112 using real-time or pre-determined computerized tomography data, in conjunction with the assembly 104 or guidewire with one or more EAM markers in the right atrium 704), intracardiac and/or transesophageal echocardiography (ICE and/or TEE) (e.g. using echogenic markers or features on the puncturing device 100).

Figure 6:
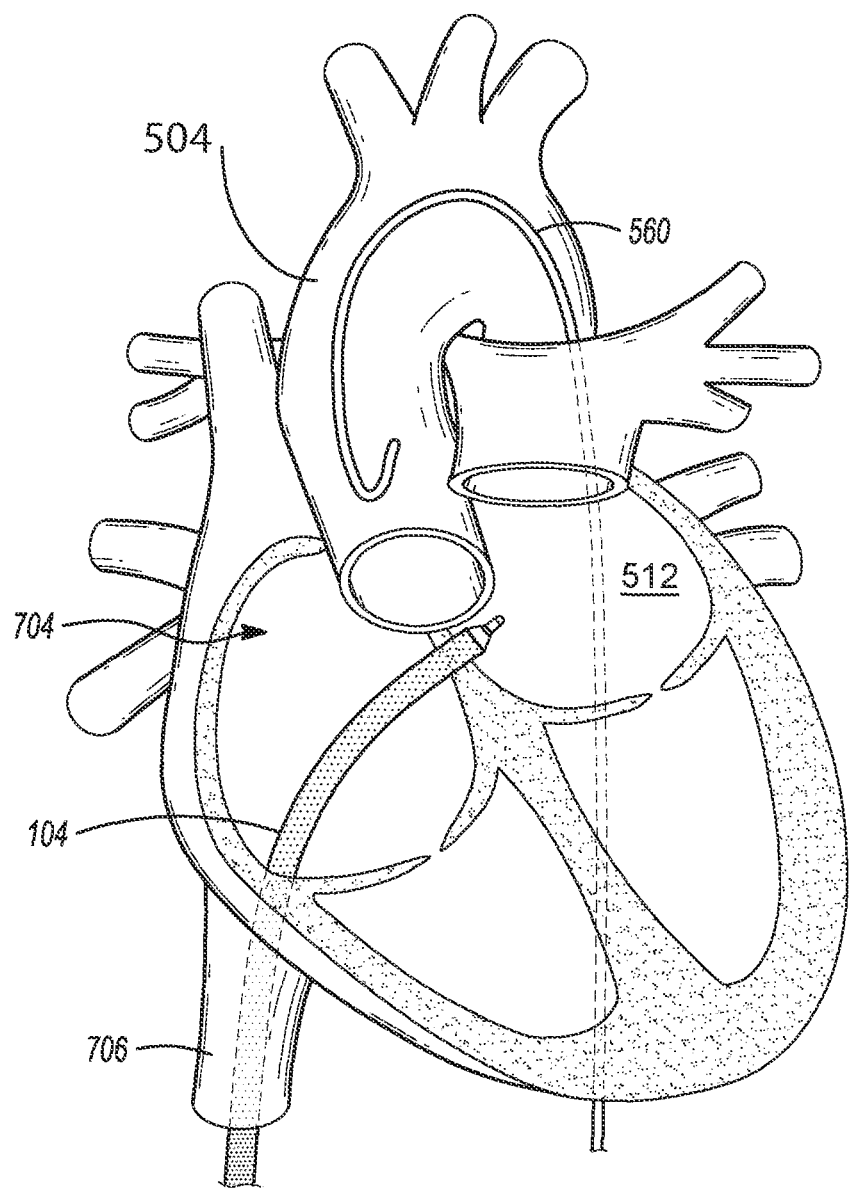
Figure 7A:
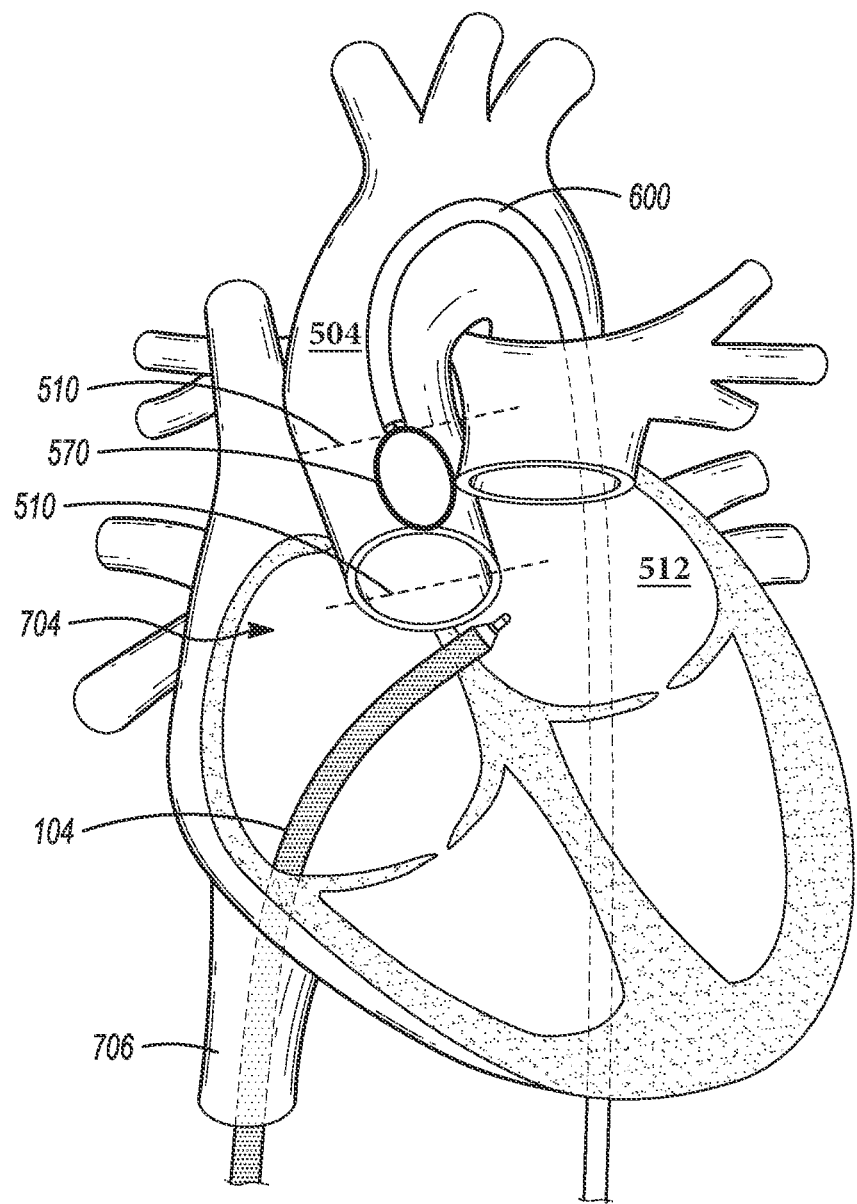

Referring to FIG. 6, as a next step (or earlier or later in the method, for example prior to the previous steps), a mechanical guidewire 560 can be placed into the ascending aorta 504 from an arterial access site (not shown). For this step, the left or right femoral artery can be percutaneously accessed (e.g., using a procedure such as a Seldinger technique). The arterial access site can be inferior or superior to the ascending aorta. The guidewire 560 can then be exchanged for a lasso catheter 600 (exemplified in FIG. 16) having a snaring loop 570 (as shown in FIG. 7A). Preferably, the snare loop 570 is aligned to approximate the Sino-Tublar Junction (STJ) 510 above the aortic valve.

Figure 7B:
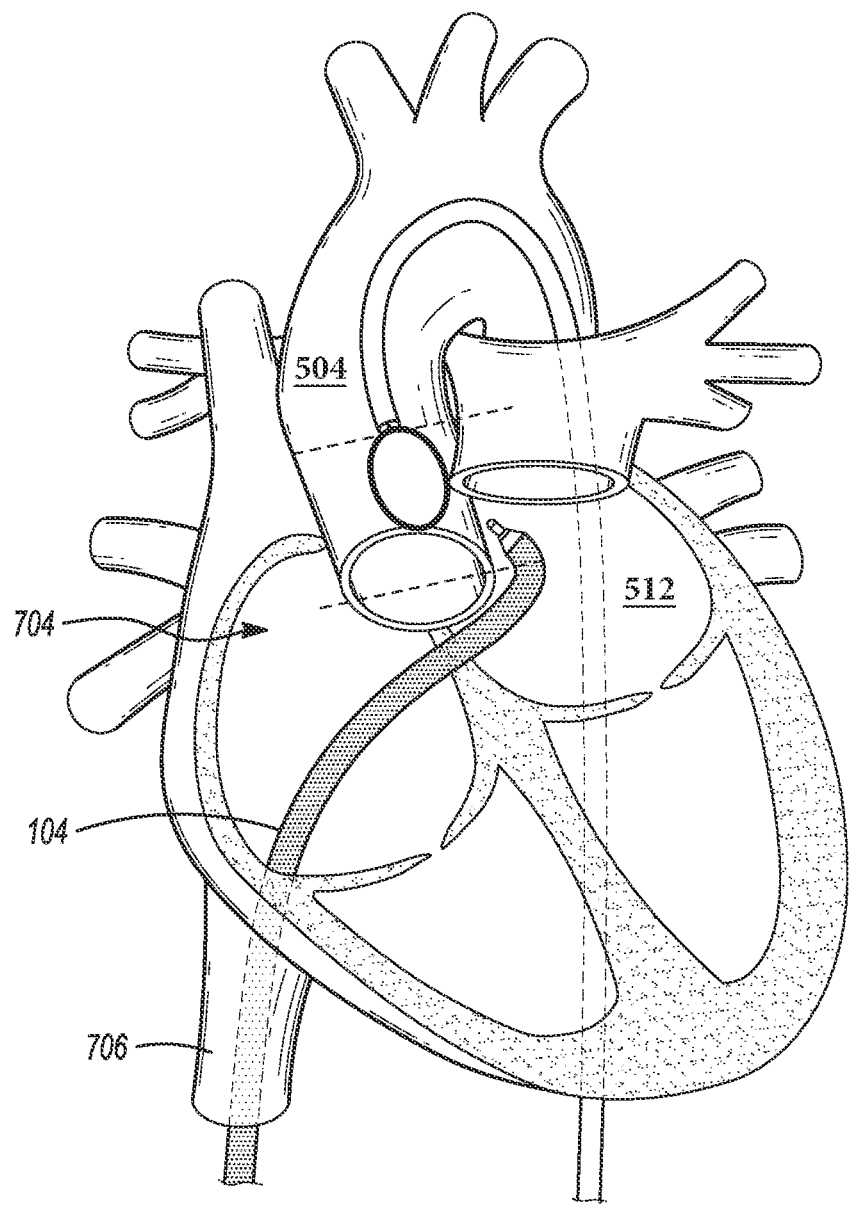
Figure 7C:
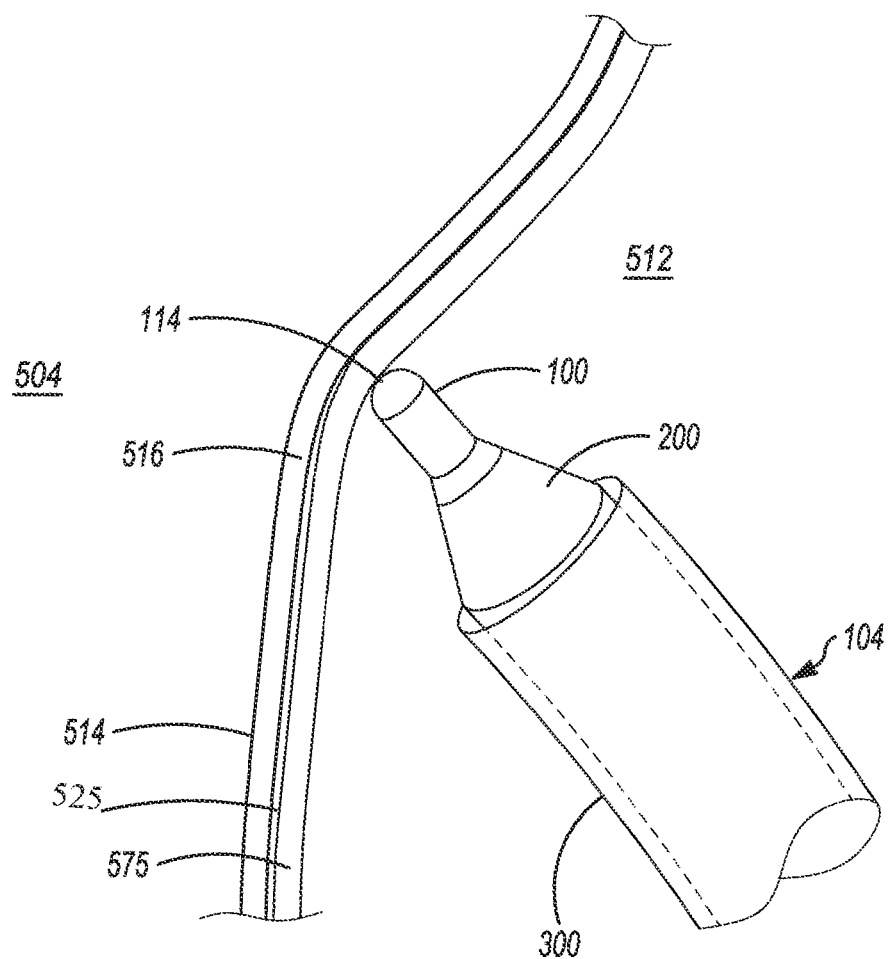

Referring to FIG. 7B, the assembly 104 of the sheath 300, dilator 200, and flexible puncturing device 100 are positioned within the left atrium 512 and directed towards the ascending aorta 504 and the puncturing target site. For example, the target site to puncture between the left atrium 512 and aorta 504 can preferably be above the Sino-Tubular Junction (STJ) 510 (as shown in FIG. 7A) which is situated above the aortic valve. In this position, the ascending aorta 504 is apposed to the left atrium 512. In this position, a space still exists between the ascending aorta 504 and left atrium 512, called the Transverse Pericardial Sinus (TPS) 525, within the pericardial space (as shown in FIG. 7C), but it is considered "virtual" or small. Support and etiology of surrounding vasculature may be used to determine an appropriate target site selection. For example, the sino-tubular junction (STJ) 510, shown in FIG. 7A, may act as an anatomical landmark and aid in positioning the assembly 104 towards the left atrium wall 575, adjacent the ascending aorta wall 514. As it would be known in the art, more superiorly into the ascending aorta 504, the aortic wall and left atrium are not apposed to each other as the aorta loops around the pulmonic trunk. After looping behind the pulmonic trunk, the aorta is referred to the "descending" aorta and apposes the left atrium again. As such, another potential puncture site is between the descending aorta 508 and left atrium free wall 575.

Once the assembly 104 is directed at the target puncturing site (as in FIG. 7B), the assembly 104 tents the tissue 516 between the left atrium wall 575 and the ascending aorta wall 514 (as seen in FIG. 7C). In order to avoid inadvertent dilation with the assembly, the dilator 200 may be retracted into the sheath 300 until the dilator 200 and sheath 300 tip are aligned; thus, the dilator 200 would still provide support to the flexible puncturing device 100 without losing the optimal puncture location. In some examples, the position of the assembly 104 may be observed using any suitable means, as previously described.

Figure 8A:
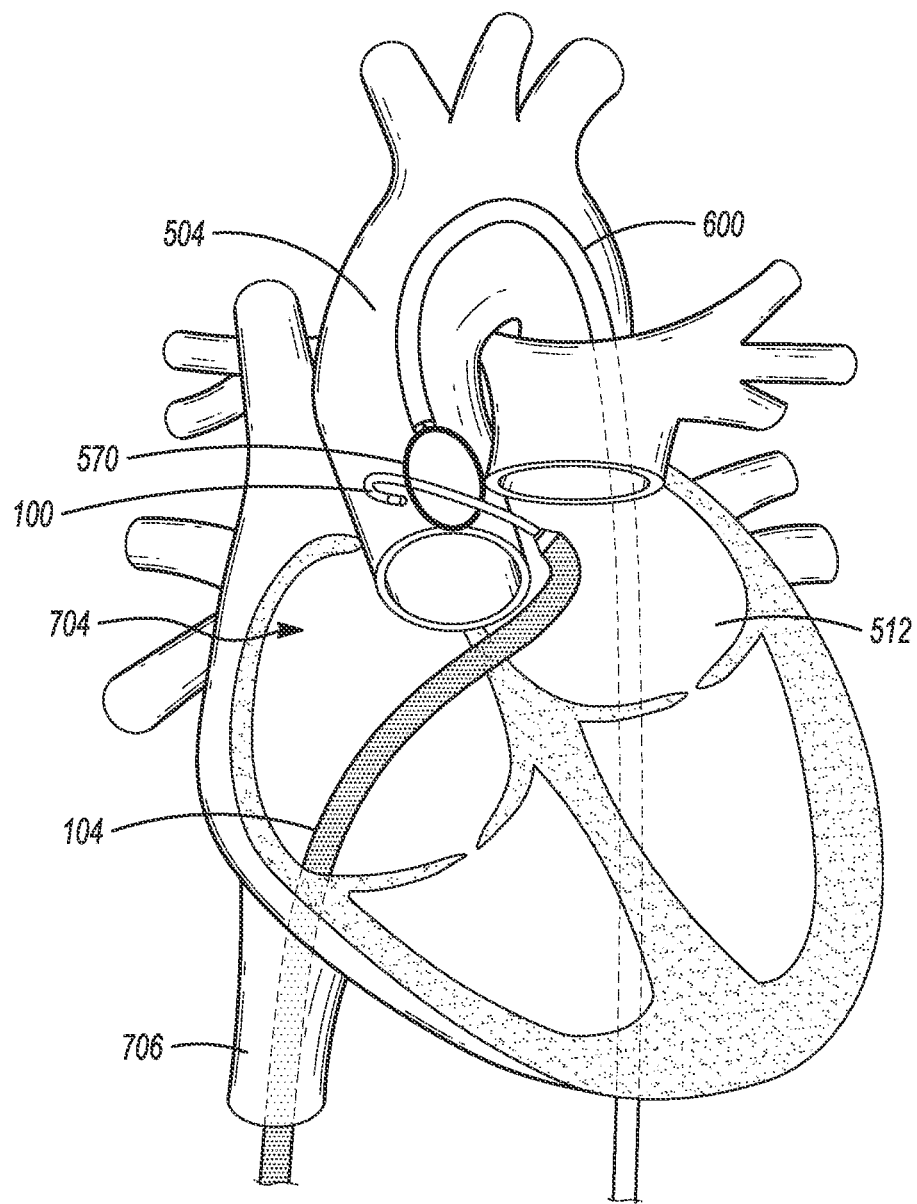

Referring to FIG. 8A, radiofrequency energy is applied to the flexible puncturing device 100 and delivered to the distal tip (perforating tip) 112 via the energy delivery device 114 for puncturing both the left atrium wall 575 and aortic wall 514. The flexible puncturing device 100 can then be advanced during energy application, creating a pathway or a hole and to allow fluid communication between the left atrium 512 and aorta 504. In some examples, creation of the pathway can be confirmed using fluoroscopy, electro-anatomical mapping, pressure measurement, contrast injection, and intracardiac and/or transesophageal echocardiography. The hole remains patent due to the puncturing device 100 (such as RF wire) occluding the hole and blood is prevented from leaking into the Transverse Pericardial Sinus 525 due to the occlusion by the device. Until the physician is ready to dilate the hole to place end therapy devices, it is preferable to not immediately dilate with the sheath and dilator assembly.

Figure 8B:
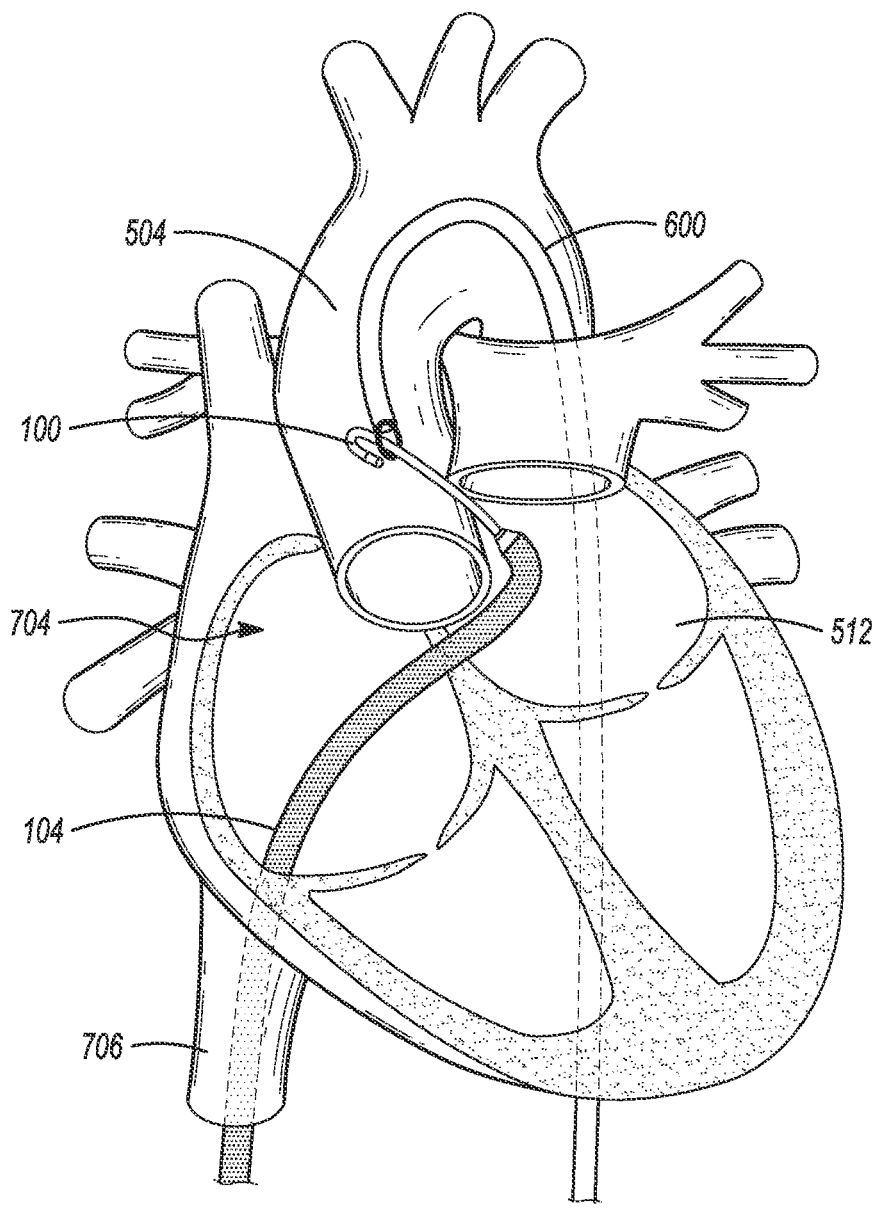
Figure 9:
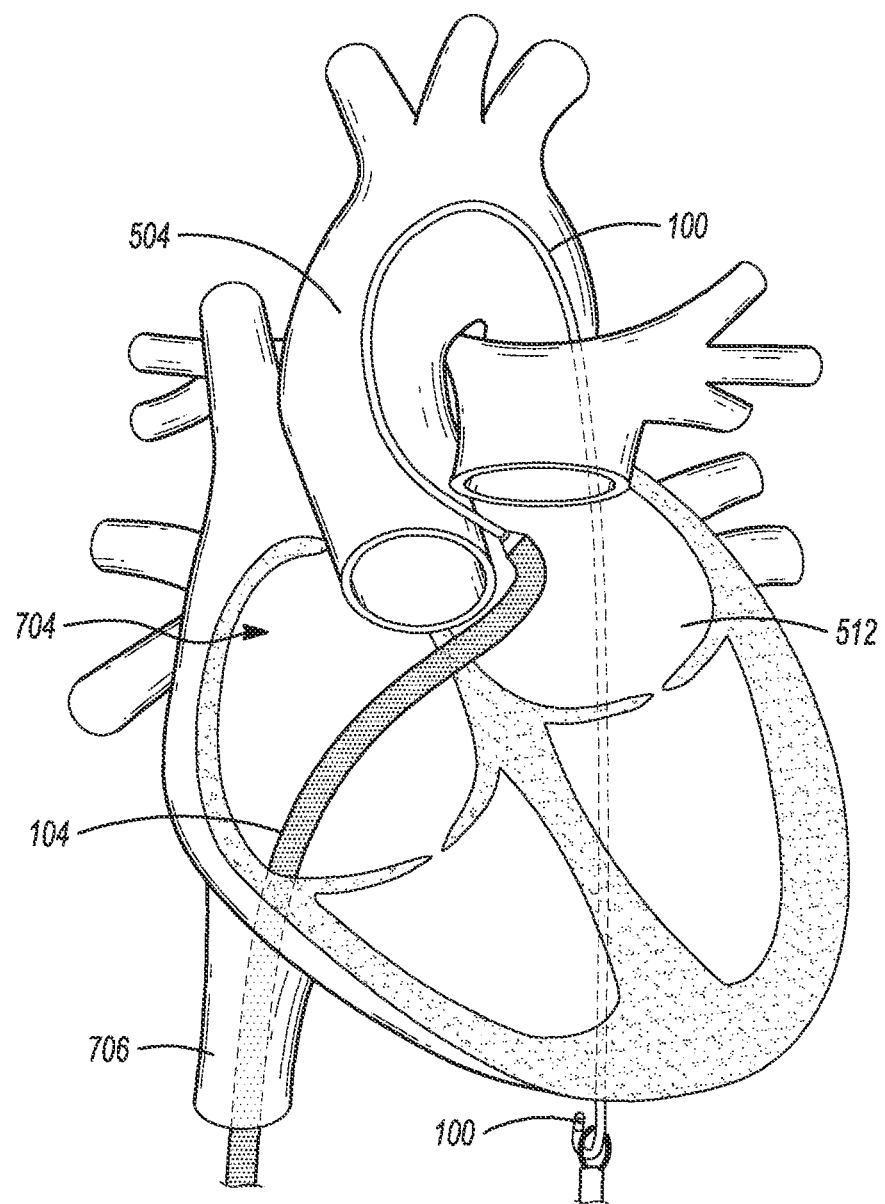
FIGS. 9 and 10 illustrates the steps of a method for externalizing the puncture device, in accordance with an embodiment of the present disclosure.
Figure 10:
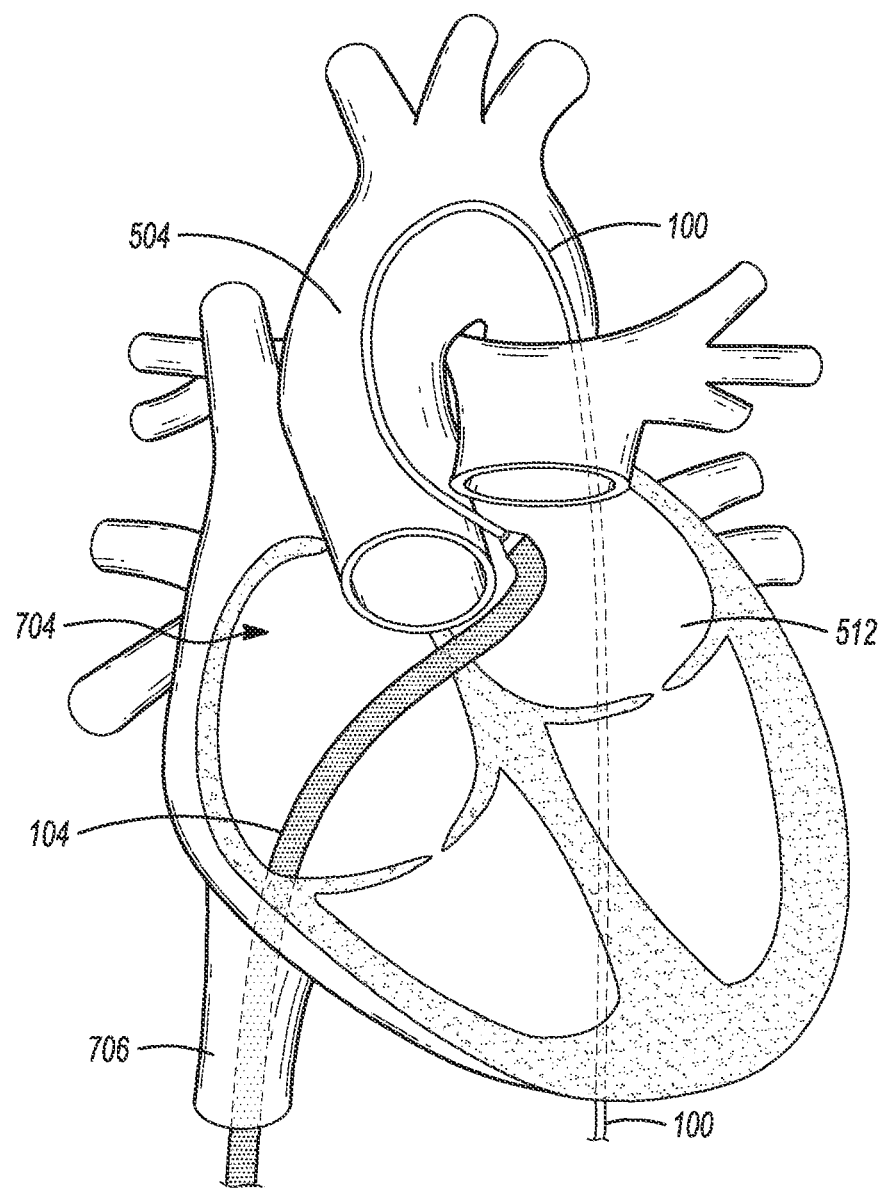

Referring to FIGS. 8A and 8B, the snare 570 of lasso catheter 600 can then be used to capture the distal end of the flexible puncturing device 100, by retraction of the snare loop into the lasso catheter sheath and "closing" on the distal end of the flexible puncturing device 100. The snare 570 can then be retracted to advance the puncturing device 100 towards the arterial access site as shown in FIG. 9 (e.g., left or right femoral artery, not shown), optionally to externalize the distal end of the flexible puncturing device 100.

Alternatively, the sheath 300 can be retracted towards femoral vein (for example, inferior vena cava 706) and a secondary sheath (e.g., a large bore sheath designed for therapeutic device delivery) can be advanced via the femoral vein. The secondary sheath can then be used to deliver a therapeutic device to the pathway.

In some embodiments, the flexible wire may be externalized to support advancement of end-therapy devices through the perforation between the aorta and the left atrium. Externalization of the flexible puncturing device 100 may be achieved through, for example, the patient's femoral artery or femoral vein. An externalized flexible wire having sufficient length may be used to support the introduction and positioning of stiffer therapeutic devices, such as end-therapy devices or end-therapy delivery devices. In this embodiment, the puncture device 100 would be dimensioned such that while the device is still accessible from the inferior entry point (for example, inferior vena cava 706) it is also externalized via the arterial access (e.g., left or right femoral artery). By allowing both ends of the puncture device 100 to be simultaneously secured by the user, the puncture device may act as a stiff support track allowing advancement of end-therapy devices through the femoral access.

In another embodiment, a method for creating a perforation from the aorta to the left atrium is illustrated in FIGS. 11 to 15. The methods disclosed herein involve the creation of a pathway between the aorta 504 and the left atrium 512 via an inferior approach—that is, the aorta can be approached via an inferior artery (e.g., the femoral artery), and a perforation can be created in the wall of the aorta and then into the wall of the left atrium. The methods disclosed result in externalizing the puncture device 100 by positioning a snare, such as a lasso catheter 600, in the left atrium 512 to capture the puncture device 100 once the puncture device enters the left atrium 512 from the aorta 504.

Figure 11:
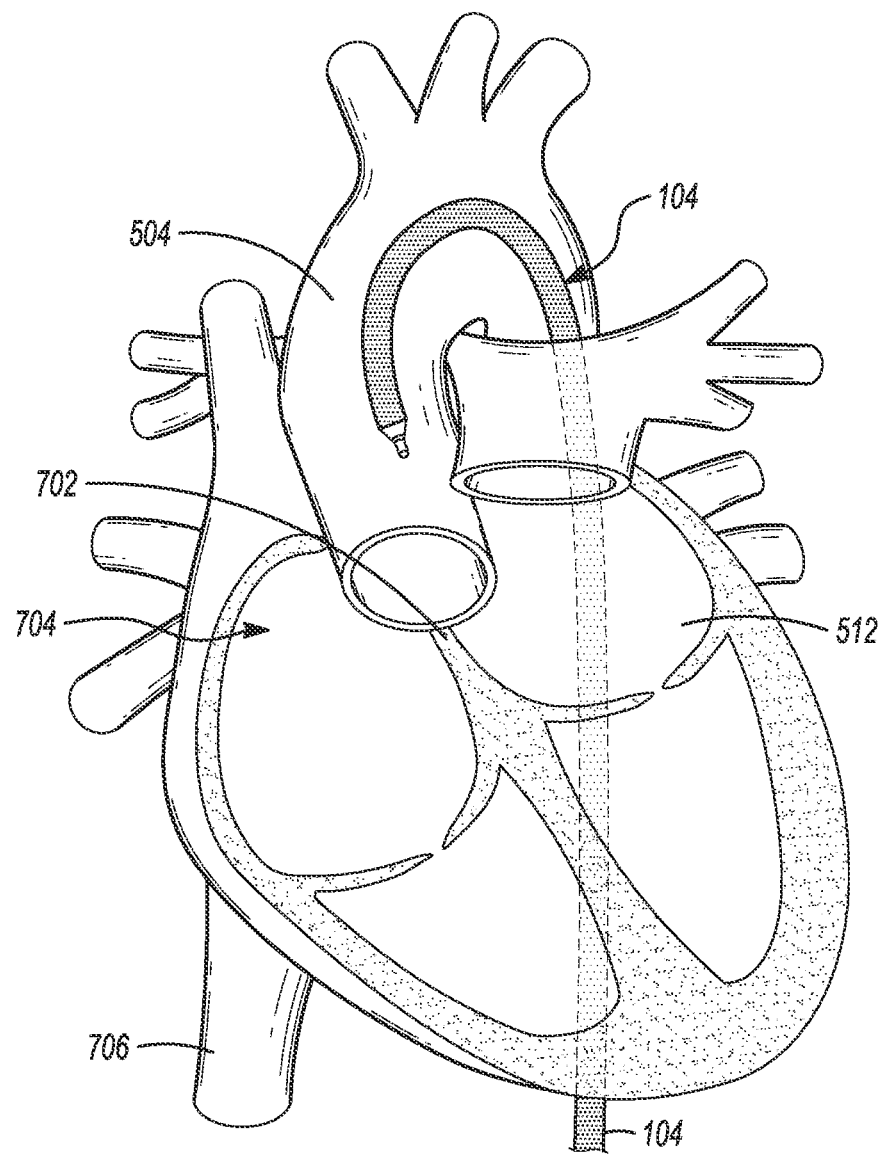
FIGS. 11, 12, and 13 illustrates the steps of a method for accessing a left atrium via an aorta, in accordance with an embodiment of the present disclosure.
Figure 12:
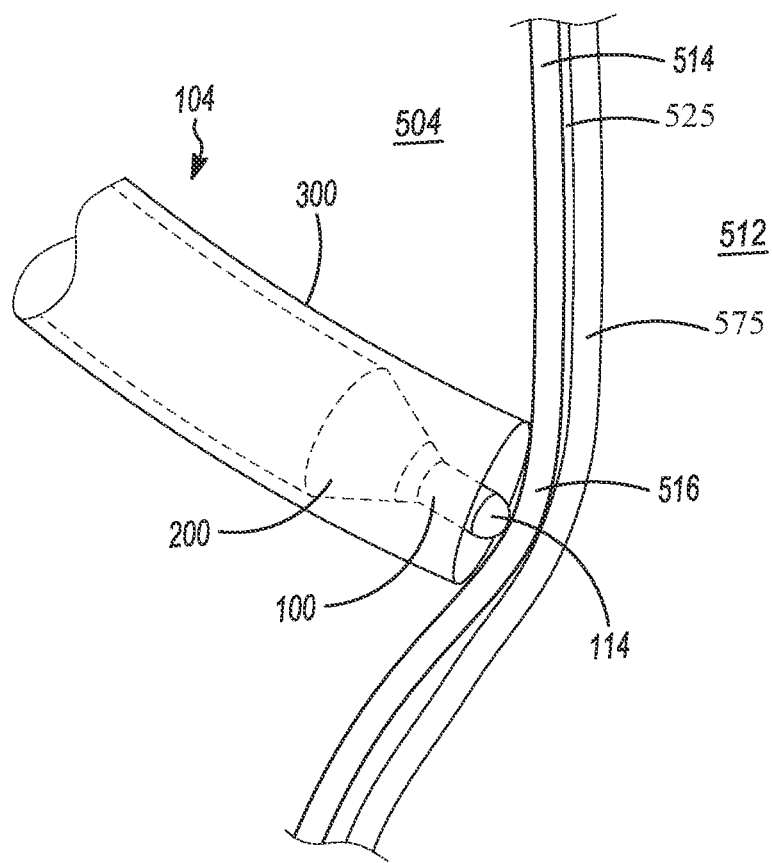

In accordance with a method aspect of this disclosure for creating a perforation from the aorta to the left atrium, the assembly 104 of the sheath 300, dilator 200, and flexible puncturing device 100 are advanced into the ascending aorta 504, as shown in FIG. 11, by first percutaneously accessing an inferior artery (for example, left or right femoral artery using a procedure such as a Seldinger technique) and advancing the perforating tip (distal tip) 112 of the puncturing device 100 into the inferior artery and towards the ascending aorta 504. The sheath 300 and the dilator 200 (such as a flexible dilator) are inserted over the puncturing device 100 until the distal tip of the flexible puncturing device 100 is aligned with the distal tip of the dilator 200. The assembly 104 of the sheath 300, dilator 200, and flexible puncturing device 100 are then positioned within the aorta, adjacent the perforation site (target site) against the aorta wall 514, as shown in FIG. 12. This can be achieved by steering the sheath 300 and/or dilator 200 (in examples wherein the sheath 300 and/or the dilator 200 are steerable), or by adjusting the position of the sheath 300 and/or dilator 200. This step can optionally be facilitated using fluoroscopy (e.g. in examples wherein the puncturing device 100 or the assembly 104 includes one or more radiopaque markers or features), angiography, electro-anatomical mapping (EAM) (e.g. to confirm real-time positioning of the perforating tip 112 using real-time or pre-determined computerized tomography data, in conjunction with a catheter or guidewire with one or more EAM markers in the aorta, intracardiac and/or transesophageal echocardiography (ICE and/or TEE) (e.g. using echogenic markers or features on the puncturing device 100 or on the sheath 300 and/or dilator 200). Alternatively, support and etiology of surrounding vasculature may be used to determine an appropriate target site selection. For example, the Sino-Tubular Junction (STJ) 510 (as shown in FIG. 7A) may act as an anatomical landmark and aid in positioning the assembly 104 towards the left atrium 512 to determine puncture site between the ascending aorta 504 and the left atrium 512. Alternatively, positioning the assembly near the left superior and inferior pulmonary veins may aid in creating communication between the descending aorta and the left atrium.

Referring to FIG. 12, the assembly 104 can then be directed at the puncturing site (site) and may tent the tissue 516 between the aorta wall 514 and left atrium wall 575. In some embodiments, the dilator 200 is retracted into the sheath 300, thereby enabling the sheath 300 to act as a stabilizer while positioning against the target tissue while enabling the dilator to provide support to the flexible puncturing device 100. This allows the forward force on the assembly 104 to be evenly distributed across the vessel (i.e., the aorta wall 514), decreasing the risk of inadvertent perforation of the tissue with the dilator or inadvertent dilation of the aorta wall 514 or left atrium wall 575. The deterrence of inadvertent puncture/dilation is important to prevent blood from leaking into the Transverse Pericardial Sinus 525, a space between the aortal wall 514 and left atrium wall 575 and is within the pericardial cavity of the heart.

Once the position of the target is confirmed, radiofrequency energy can then be applied to the flexible puncturing device 100 and delivered to the tissue via the energy delivery device 114 to create the perforation. The flexible puncturing device 100 is advanced during energy application, creating a puncture between the aorta and left atrium, forming a pathway for fluid communication between the aorta and the left atrium. In an alternative embodiment, the puncturing device 100 may comprise a sharp distal tip which may be used to mechanically puncture the tissue. Confirmation of target site and access into the left atrium from the aorta may be achieved through various methods described above, including fluoroscopy, electro-anatomical mapping (EAM), pressure differentials between the aorta and left atrium, contrast injection, or using intracardiac echocardiography (ICE) or transesophageal echocardiography (TEE).

Figure 13:
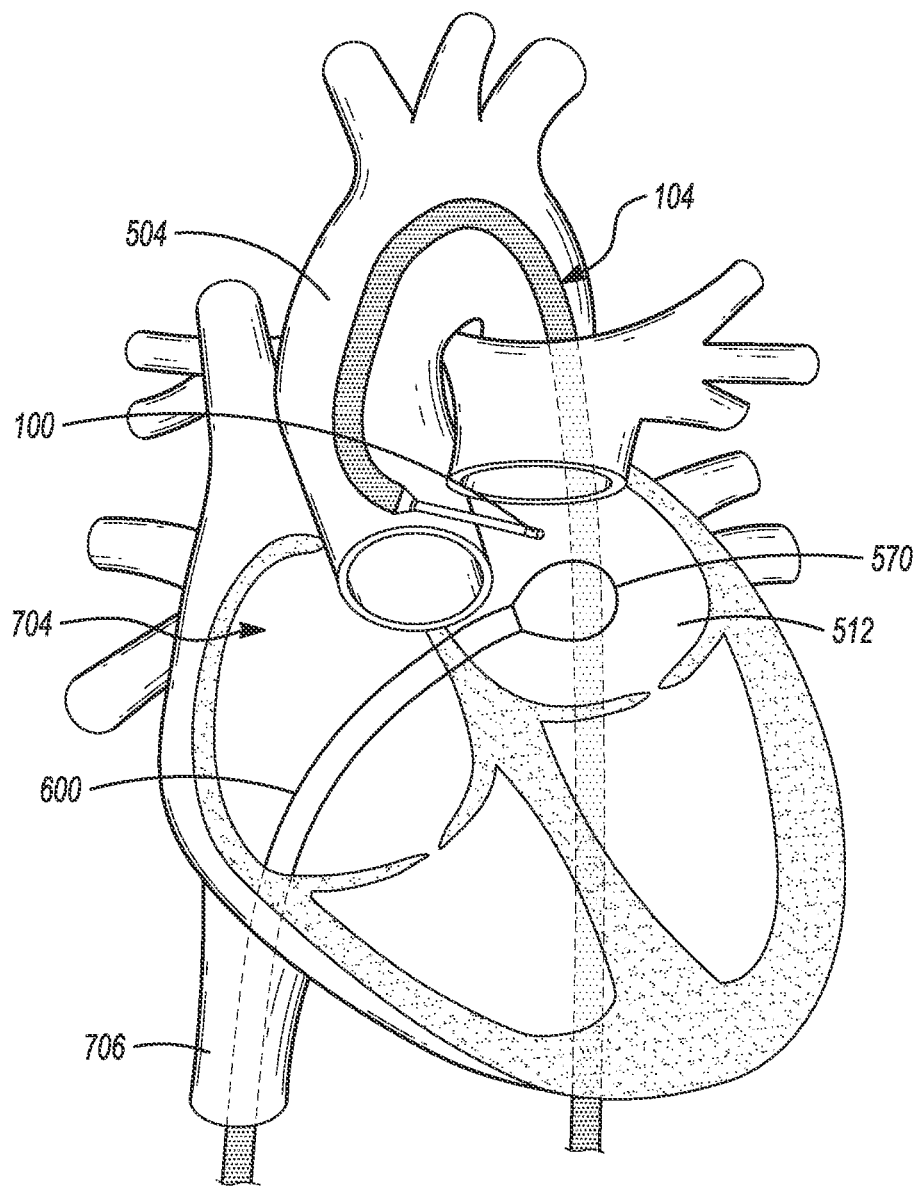

Referring to FIG. 13, with the puncturing device 100 situated within the left atrium 512, the dilator 200 may be advanced, over the flexible puncturing device 100, through the puncture site to dilate the tissue and enlarge the puncture site. The sheath 300 and flexible dilator 200 may optionally be removed, leaving the flexible puncturing device 100 within the left atrium 512 to act as a guiderail for advancing end-therapy devices into the left atrium 512. In some examples, the sheath may be advanced into the left atrium, over the flexible puncturing device, if the access sheath is able to support the delivery of the end-therapy devices.

Figure 14:
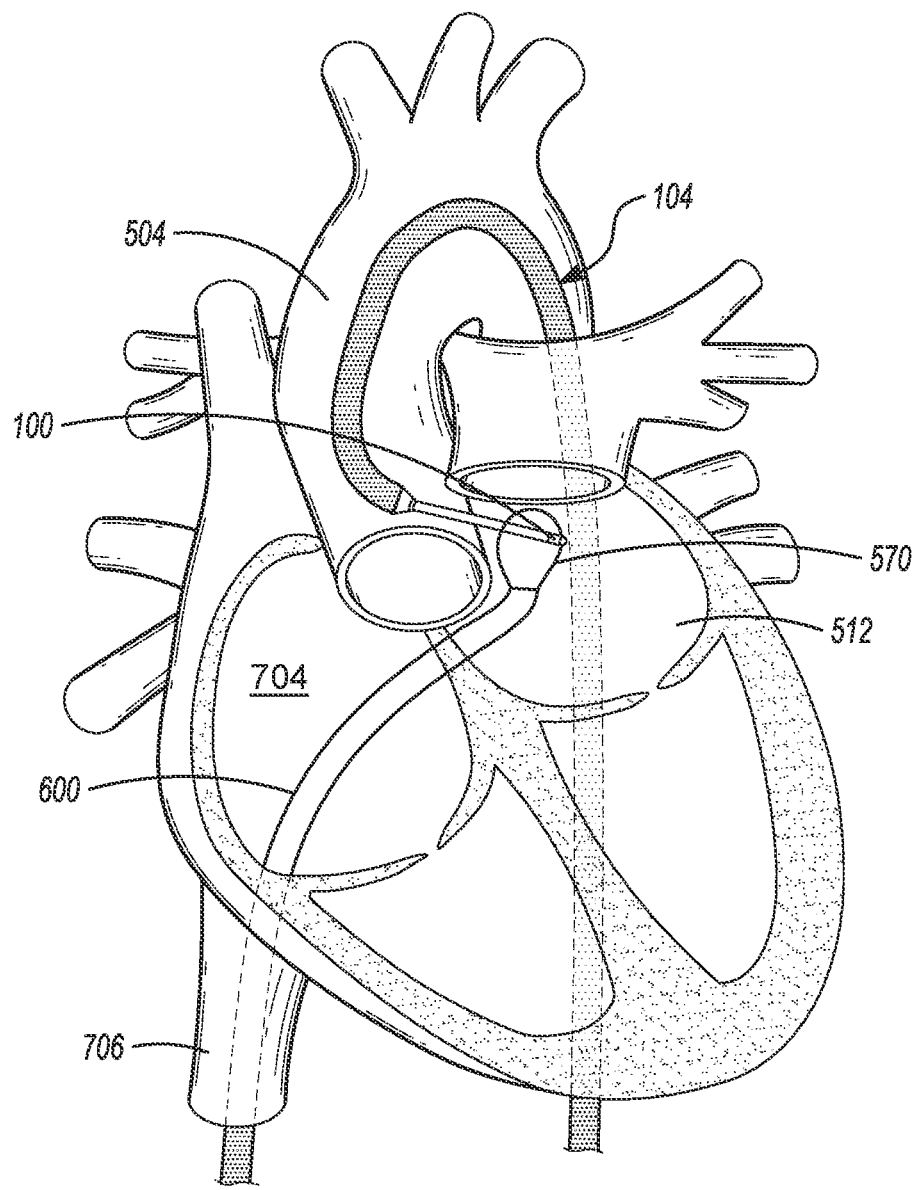
FIGS. 14 and 15 illustrates the steps of an alternative method for externalizing the puncture device in accordance with an alternative embodiment of the present disclosure.

Referring to FIGS. 13 and 14, as a next step (or earlier or later in the method, for example prior to the previous steps—prior to advancing the assembly 104 towards the ascending aorta), a snare, such as a lasso catheter 600, can be advanced towards the left atrium 512. The lasso catheter 600 can be advanced, for example, via a femoral vein (for example, inferior vena cava 706). In the example shown, the lasso catheter 600 is advanced via the inferior vena cava 706, the right atrium 704, and to the left atrium 512 via a standard transseptal procedure (described above in this disclosure), until the lasso catheter 600 reaches the left atrium 512, as shown in FIG. 13. In some examples, a physician may first gain access to the femoral vein wherein a guidewire is inserted and advanced into the right atrium via the inferior vena cava 706. The guidewire may then act as a rail for the delivery of the assembly 104 (i.e., a transseptal needle, dilator, and sheath) which may be used to cross the septum. Alternatively, a puncturing guidewire (e.g., using radiofrequency energy or mechanical force) may be used instead of a standard guidewire. Using the transseptal assembly, the physician can gain access from the right atrium into the left atrium. The physician may remove the transseptal devices and advance a lasso catheter 600 into the left atrium 512. Preferably, this step may occur before the flexible puncture device 100, sheath 300 and dilator 200 have been advanced into the ascending aorta 504, such that the lasso catheter 600 is present within the left atrium 512 and acts as a "landing zone" when the puncturing device 100 enters the left atrium 512 from the aorta 504.

Figure 15:
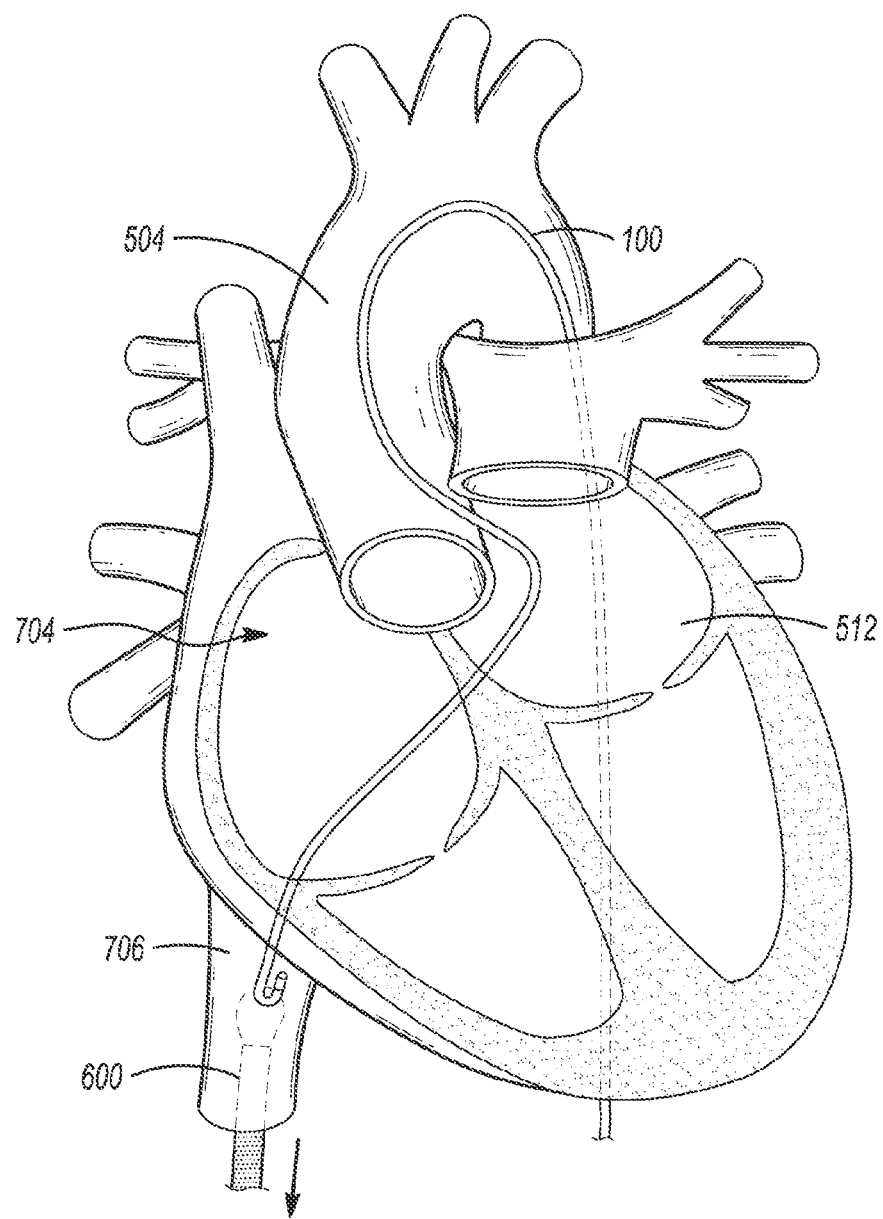
Figure 16:
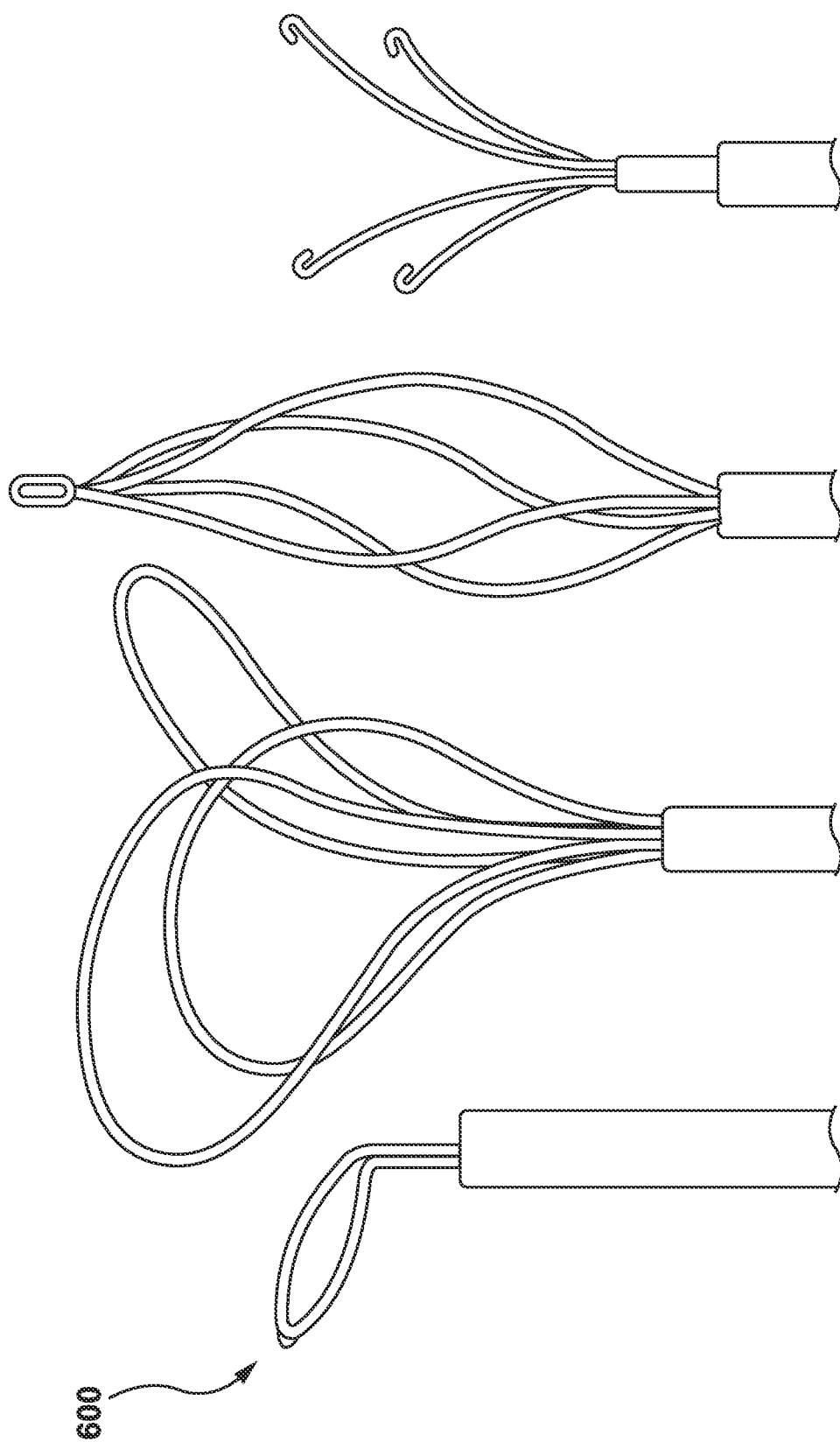
FIG. 16 illustrates an example of a lasso catheter, in accordance with an embodiment of the present disclosure.

Referring to FIG. 14, with the lasso catheter 600 in the left atrium, the snare 570 of lasso catheter 600 can then be used to capture the distal end of the flexible puncturing device 100, by retraction of the snare loop into the lasso catheter sheath and "closing" on the distal end of the flexible puncturing device 100. The lasso catheter 600 may then retract back towards the right atrium 704, pulling the puncture device 100 along with it. At this point, the sheath 300 and dilator 200 may optionally be withdrawn from the aorta. The lasso catheter 600 can then be retracted to advance the puncturing device 100 towards the venous access site, as shown in FIG. 15, optionally to externalize the distal end of the flexible puncturing device 100. Optionally, the flexible puncturing device 100 can be "flossed" to enlarge the pathway. In this example, with the lasso catheter 600 and flexible puncturing device 100 externalized outside of the arterial access sites the physician now has an externalized rail to advance large delivery sheaths over-top of the device 100 or use puncture device 100 as a stiff guiderail for the delivery of end therapy devices. By allowing both ends of the puncture device to be simultaneously secured by the user, the puncture device may act as a stiff support track allowing advancement of end-therapy devices through the femoral access.

The present disclosure in various embodiments thus provides a system and method for the creation of a pathway or communication (including for example a perforation an atrial septum and perforation between an aorta and a left atrium). Visualization techniques as disclosed herein are advantageous for positioning the assembly 104 (puncturing device 100, dilator 200, sheath 300 and/or lasso catheter 600) within a patient's heart and for confirming that the desired ancillary device has entered into the aorta, the left atrium or right atrium subsequent to perforation or puncture. It should be noted, however, that a method of the present disclosure may be practised without any or all of pressure monitoring or visualization and is thus intended to comprise a method of creating a perforation/crossing in a tissue utilizing any intravascular approach. One of the motivations for creating a pathway or communication between the aorta and left atrium is to facilitate the study or placement of end-therapy devices. In some examples, the methods of the present disclosure may be used to create a pathway or communication between the aorta and the left atrium to position a stent, a shunt, or a pressure-sensitive catheter in the pathway. The method and system of the present disclosure may also be used to create large perforations between the atria and between the left atrium and aorta, as well as other perforations between other heart chambers and heart regions. All the applications/methods and devices disclosed herein are intended to be exemplary only and are not intended to limit the scope of the present disclosure in any way.

While the above description provides examples of one or more processes or apparatuses or compositions, it will be appreciated that other processes or apparatuses or compositions may be within the scope of the accompanying claims.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

We claim:

1. A method for creating a pathway between an aorta and a left atrium of a patient's heart, comprising:
   a. via a femoral venous access site and a right atrium, advancing a puncture assembly device towards an interatrial septum, wherein said puncture assembly device comprises a sheath, a dilator, and a flexible puncturing device;
   b. positioning a perforating tip of puncturing device adjacent an interatrial septum proximate a left atrium;
   c. advancing the perforating tip to perforate through the interatrial septum creating a pathway between the right atrium and left atrium;
   d. advancing the puncturing device to the left atrium;
   e. advancing the sheath and the dilator over the puncturing device through the septum and into the left atrium such that perforating tip of the puncturing device is aligned with a distal tip of the sheath and a distal tip of the dilator, forming said puncturing assembly;
   f. positioning the puncturing assembly at a target site within the left atrium to gain access to the aorta;
   g. advancing the perforating tip of the puncturing device to perforate through the wall of the left atrium and then through a wall of the aorta, to create a pathway between the aorta and the left atrium;
   h. advancing a snare towards the aorta via an arterial access site;
   i. snaring the puncturing device with the snare; and
   j. confirming the creation of the pathway between the aorta and the left atrium with at least one of fluoroscopy, electro-anatomical mapping, pressure measurement, contrast injection, and echocardiography.

2. The method of claim 1, wherein the puncturing device is a radiofrequency puncturing device, the perforating tip comprises a radiofrequency perforation electrode, and step
   g. comprises delivering radiofrequency energy from the radiofrequency perforation electrode while advancing the perforating tip.

3. The method of claim 1, further comprising:
   h. after step g., advancing a dilating tip of the dilator over the perforation device and through the pathway to dilate the pathway between the aorta and the left atrium; and step i. retracting the dilator through the sheath.

4. The method of claim 3, wherein the sheath is selected from a steerable sheath, a fixed curve sheath, a small-bore steerable sheath, a large-bore steerable sheath, or a telescoping steerable sheath, and the dilator is a flexible dilator.

5. The method of claim 3, further comprising:
   j. after step i., delivering a therapeutic device to the pathway via the sheath.

6. The method of claim 5, wherein step j. comprises positioning a shunt or a stent in the pathway.

7. The method of claim 1, further comprising:
   j. after step i., retracting the snare to advance the puncturing device out of the body towards the arterial access site.

8. The method of claim 7, further comprising delivering a therapeutic device over the puncturing device towards the pathway, via the arterial access site.

9. The method of claim 1, wherein at least one of fluoroscopy, angiography, electro-anatomical mapping, intracardiac echocardiography, and transesophageal echocardiography is carried out concurrently with at least one of steps a. to g.

10. A method for creating a pathway between an aorta and a left atrium of a patient's heart, comprising:
    a. via a femoral venous access site and a right atrium, advancing a puncture assembly device towards an interatrial septum, wherein said puncture assembly device comprises a sheath, a dilator, and a flexible puncturing device;
    b. positioning a perforating tip of puncturing device adjacent an interatrial septum proximate a left atrium;
    c. advancing the perforating tip to perforate through the interatrial septum creating a pathway between the right atrium and left atrium;
    d. advancing the puncturing device to the left atrium;
    e. advancing the sheath and the dilator over the puncturing device through the septum and into the left atrium such that perforating tip of the puncturing device is aligned with a distal tip of the sheath and a distal tip of the dilator, forming said puncturing assembly;
    e. advancing the perforating tip of the puncturing device to perforate through the wall of the left atrium and then through a wall of the aorta, to create a pathway between the aorta and the left atrium;
    f. positioning the puncturing assembly at a target site within the left atrium to gain access to the aorta;

g. advancing the perforating tip of the puncturing device to perforate through the wall of the left atrium and then through a wall of the aorta, to create a pathway between the aorta and the left atrium;
h. advancing a dilating tip of the dilator over the perforation device and through the pathway to dilate the pathway between the aorta and the left atrium; and step i. retracting the dilator through the sheath;
i. delivering a therapeutic device to the pathway via a large-bore steerable sheath; and
j. exchanging the sheath for a large-bore steerable sheath.

11. A method for creating a pathway between an aorta and a left atrium of a patient's heart, comprising:
a. via a femoral venous access site and a right atrium, advancing a puncture assembly device towards an interatrial septum, wherein said puncture assembly device comprises a sheath, a dilator, and a flexible puncturing device;
b. positioning a perforating tip of puncturing device adjacent an interatrial septum proximate a left atrium;
c. advancing the perforating tip to perforate through the interatrial septum creating a pathway between the right atrium and left atrium;
d. advancing the puncturing device to the left atrium;
e. advancing the sheath and the dilator over the puncturing device through the septum and into the left atrium such that perforating tip of the puncturing device is aligned with a distal tip of the sheath and a distal tip of the dilator, forming said puncturing assembly;
f. positioning the puncturing assembly at a target site within the left atrium to gain access to the aorta;
g. advancing the perforating tip of the puncturing device to perforate through the wall of the left atrium and then through a wall of the aorta, to create a pathway between the aorta and the left atrium;
h. advancing a snare towards the aorta via an arterial access site; and
i. snaring the puncturing device with the snare.

* * * * *